United States Patent
Georgeson et al.

(10) Patent No.: US 10,191,478 B2
(45) Date of Patent: Jan. 29, 2019

(54) SYSTEMS AND METHODS FOR NON-DESTRUCTIVE TESTING INVOLVING REMOTELY LOCATED EXPERT

(71) Applicant: The Boeing Company, Chicago, IL (US)

(72) Inventors: Gary E. Georgeson, Tacoma, WA (US); Tyler M. Holmes, Seattle, WA (US); Jeffrey R. Kollgaard, Seattle, WA (US)

(73) Assignee: The Boeing Company, Chicago, IL (US)

( * ) Notice: Subject to any disclaimer, the term of this patent is extended or adjusted under 35 U.S.C. 154(b) by 412 days.

(21) Appl. No.: 14/741,393

(22) Filed: Jun. 16, 2015

(65) Prior Publication Data

US 2016/0370798 A1 Dec. 22, 2016

(51) Int. Cl.
*G05B 23/00* (2006.01)
*G01N 29/24* (2006.01)

(52) U.S. Cl.
CPC ......... *G05B 23/00* (2013.01); *G01N 29/2481* (2013.01); *G01N 2291/2694* (2013.01)

(58) Field of Classification Search
CPC ............................ G05B 23/00; G01N 29/2481
USPC ........................................................ 702/188
See application file for complete search history.

(56) References Cited

U.S. PATENT DOCUMENTS

| | | | |
|---|---|---|---|
| 8,019,504 B2 | 9/2011 | Jamrosz et al. | |
| 8,255,170 B2 | 8/2012 | Kollgaard et al. | |
| 8,291,043 B2 | 10/2012 | Hadley et al. | |
| 8,446,305 B1* | 5/2013 | Zanoni | H03M 1/124 341/137 |
| 8,825,498 B2 | 9/2014 | Kollgaard | |
| 2008/0109187 A1 | 5/2008 | Kollgaard et al. | |
| 2008/0301152 A1 | 12/2008 | Kollgaard et al. | |
| 2012/0327187 A1 | 12/2012 | Troy et al. | |
| 2013/0278365 A9* | 10/2013 | Gravendeel | A43B 1/0054 335/219 |
| 2013/0278635 A1* | 10/2013 | Maggiore | G06T 19/006 345/633 |

(Continued)

FOREIGN PATENT DOCUMENTS

| | | | |
|---|---|---|---|
| EP | 1168121 A2 | 1/2002 | |
| EP | 2538241 A2 | 12/2012 | |

OTHER PUBLICATIONS

Abd El-Ghany et al., "AutoNDT: new software for remote ultrasonic scanning via the Internet", NDT&E International, vol. 35, No. 1 (Jan. 1, 2002), p. 1-8.

(Continued)

*Primary Examiner* — Marc Armand
(74) *Attorney, Agent, or Firm* — Ostrager Chong Flaherty & Broitman P.C.

(57) ABSTRACT

An integrated and networked system of remote operations is provided that extends remote expert NDT methodology to a variety of manufacturing and in-service processes. The functional elements of the system comprise remote NDT applications, advanced remote NDT, remote administration, remote NDT commercial operations, and remote data analytics, which are all tied together by a remote communications hub. The communications hub has communication links with computer systems of those functional elements.

19 Claims, 13 Drawing Sheets

(56) References Cited

U.S. PATENT DOCUMENTS

2014/0207875 A1* 7/2014 Messinger ............ H04L 65/403
709/206

OTHER PUBLICATIONS

Extended European Search Report in European Application No. 16174453.7 (European counterpart of the instant application) dated Oct. 31, 2016.

* cited by examiner

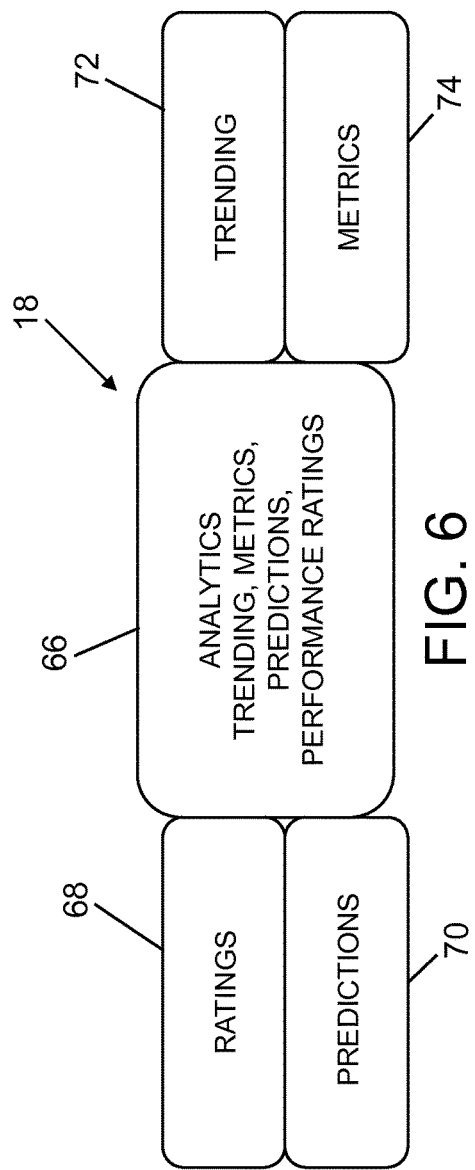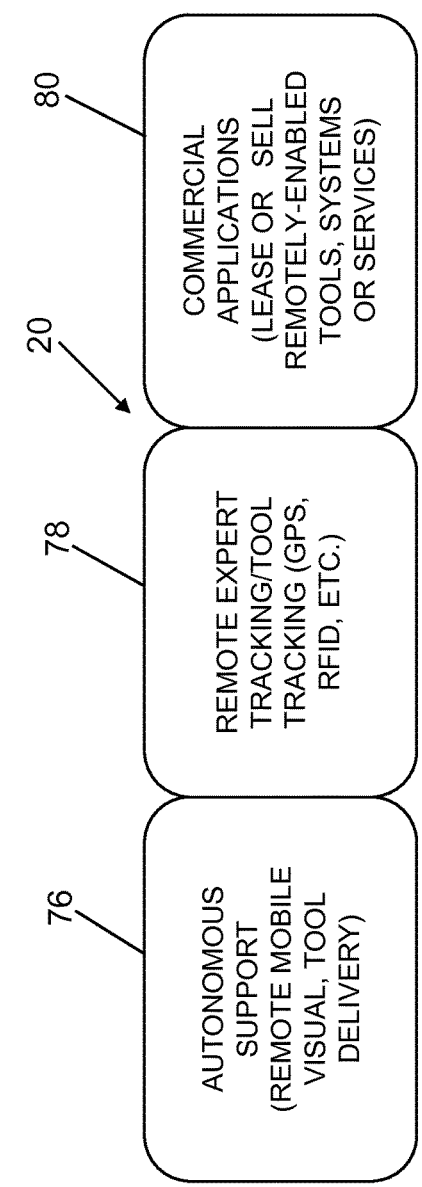

SYSTEMS AND METHODS FOR NON-DESTRUCTIVE TESTING INVOLVING REMOTELY LOCATED EXPERT

BACKGROUND

This invention generally relates to systems and methods for non-destructive testing (NDT) of manufactured articles, and in particular, to systems and methods for non-destructive testing of articles (e.g., aircraft) by an off-site NDT expert.

Aircraft maintenance involves analysis and actions to maintain and/or improve the airworthiness and reliability of an aircraft and its systems, subsystems, and components throughout its life cycle. Such actions may include the development of aircraft maintenance programs comprising specifications concerning proper inspection and repair procedures. Monitoring, control, and/or implementation of airworthiness directives issued by aviation regulatory authorities for an aircraft also may be performed as part of aircraft maintenance.

Further, aircraft maintenance may also include performing one or more of overhaul, repair, inspection, replacement, modification, or other suitable actions with respect to an aircraft part. These actions may be performed as part of an aircraft maintenance program. Further, aircraft maintenance also may include conducting periodic inspections (e.g., non-destructive inspections) based on calendar time, time in service, flight cycles, and/or landing cycles. However, oftentimes unplanned maintenance is called for.

Non-destructive testing and results analysis of manufactured articles (such as aircraft) preferably includes participation by specially trained NDT experts. Some prior processes specified that an NDT expert be present at the site where a test article (e.g., an airplane) was undergoing non-destructive inspection. It is advantageous to have an expert provide guidance and feedback during the entire inspection process, yet it is costly to have a seasoned NDT expert on site for each inspection.

It would be advantageous to provide systems and methods for NDT that eliminate the need for on-site experts to conduct an inspection of an aircraft structure and make a repair decision. Such systems and methods would reduce maintenance costs for composite aircraft by increasing the productivity of the participating experts, reducing their travel expenses, and reducing out-of-service costs of the airplane while experts travel to the inspection site.

SUMMARY

The subject matter disclosed in detail below comprises systems and methods which facilitate on-site non-destructive inspections conducted by off-site (i.e., remote) NDT experts by networking related processes together. (As used herein, non-destructive testing includes data acquisition during a non-destructive inspection and subsequent evaluation of the acquired inspection data.) The systems and methods disclosed herein provide an integrated and networked solution that takes advantage of recent technological advances in remote operations, mobile platforms, cell phones, data mining, and data analytics.

In accordance with one or more embodiments, an integrated and networked system of remote operations is provided that extends remote expert NDT methodology to a variety of manufacturing and in-service processes. The functional elements of the system comprise remote NDT applications, advanced remote NDT, remote administration, remote NDT commercial operations, and remote data analytics, which are all tied together by a remote communications hub. The communications hub has communication links with computer systems of those functional elements.

One aspect of the subject matter disclosed in detail below is a remote expert non-destructive testing system comprising a remote communications hub and a multiplicity of non-destructive testing equipment located at respective testing sites and networked to the remote communications hub by respective communication links. The remote communications hub may comprise a multiplicity of computers and a network interconnecting the multiplicity of computers. In accordance with various embodiments, the remote communications hub comprises a security system configured to limit access to the system. The remote communications hub comprises a database storing non-destructive testing data acquired by the multiplicity of non-destructive testing equipment.

The remote expert non-destructive testing system described in the preceding paragraph may further comprise a computer system networked to the remote communications hub, wherein the computer system is programmed to execute one or more of the following processes: defect recognition based on non-destructive testing data received from the remote communications hub; modeling of structures and flaws in three-dimensional space based on non-destructive testing data received from the remote communications hub; analysis of non-destructive testing data received from the remote communications hub; determining a location of an expert and sending expert location information to the remote communications hub; determining a location of a tool and sending tool location information to the remote communications hub; and tracking a mobile platform and sending mobile platform location information to the remote communications hub.

Another aspect of the subject matter disclosed herein is a method for operating a remote expert non-destructive testing system, comprising: sending guidance from a remote communications hub to an inspection site; performing non-destructive testing of a structure using non-destructive testing equipment located at the inspection site in accordance with the guidance; sending non-destructive testing data acquired during the non-destructive testing from the inspection site to the remote communications hub; storing the non-destructive testing data at the remote communications hub; sending the non-destructive testing data from the remote communications hub to a first computer system programmed to process non-destructive testing data; and processing the non-destructive testing data using a computer program hosted on the first computer system. The processing may comprise one or more of the following: recognizing defects based on the non-destructive testing data received from the remote communications hub; modeling structures and flaws in three-dimensional space based on the non-destructive testing data received from the remote communications hub; or analyzing the non-destructive testing data received from the remote communications hub. The method may further comprise: storing digital representations of procedures, specifications, standards, and training instructions in a database at a location that is not part of the remote communications hub; and sending a digital representation from the database to the remote communications hub in response to a request from the remote communications hub, wherein the guidance comprises the digital representation received by the remote communications hub. In addition or in the alternative, the method may further comprise: sending equipment location data from the inspection site to a second computer system programmed to track locations of equipment; and tracking locations of equipment using a computer program hosted on the second computer system; and sending equipment location information from the second computer system to the remote communications hub in response to a request from the remote communications hub. In addition or in the alternative, the method may further comprise: monitoring states of the non-destructive testing equipment located at the inspection site; and uploading a software upgrade to equipment at the inspection when the monitoring indicates that an upgrade is due.

A further aspect of the subject matter disclosed herein is a remote communications hub comprising a computer system programmed to perform the following operations: receiving non-destructive testing data from multiple inspection sites; classifying the received non-destructive testing data; storing the classified non-destructive testing data in memory; monitoring various parameters indicative of a state of operation of the remote communications hub; and blocking unauthorized access to stored non-destructive testing data. In some embodiments, the monitoring comprises monitoring states of non-destructive testing equipment located at the inspection sites, and the computer system is further programmed to upload a software upgrade to equipment at an inspection site when the monitoring indicates that an upgrade is due.

Other aspects of systems and processes for NDT of structural components by a remotely located expert are disclosed below.

BRIEF DESCRIPTION OF THE DRAWINGS

FIG. 4 is a diagram identifying categories of advanced remote NDT which may be included in the remote expert NDT system diagrammed in FIG. 1, which processes are used when precise locating of an activity relative to a structure being inspected is called for.

FIG. 6 is a diagram identifying categories of functions performed by a remote data analytics element of the remote expert NDT system diagrammed in FIG. 1.

FIG. 7 is a diagram identifying categories of commercial services available from a remote NDT profit center of the remote expert NDT system diagrammed in FIG. 1.

Reference will hereinafter be made to the drawings in which similar elements in different drawings bear the same reference numerals.

DETAILED DESCRIPTION

Figure 1:
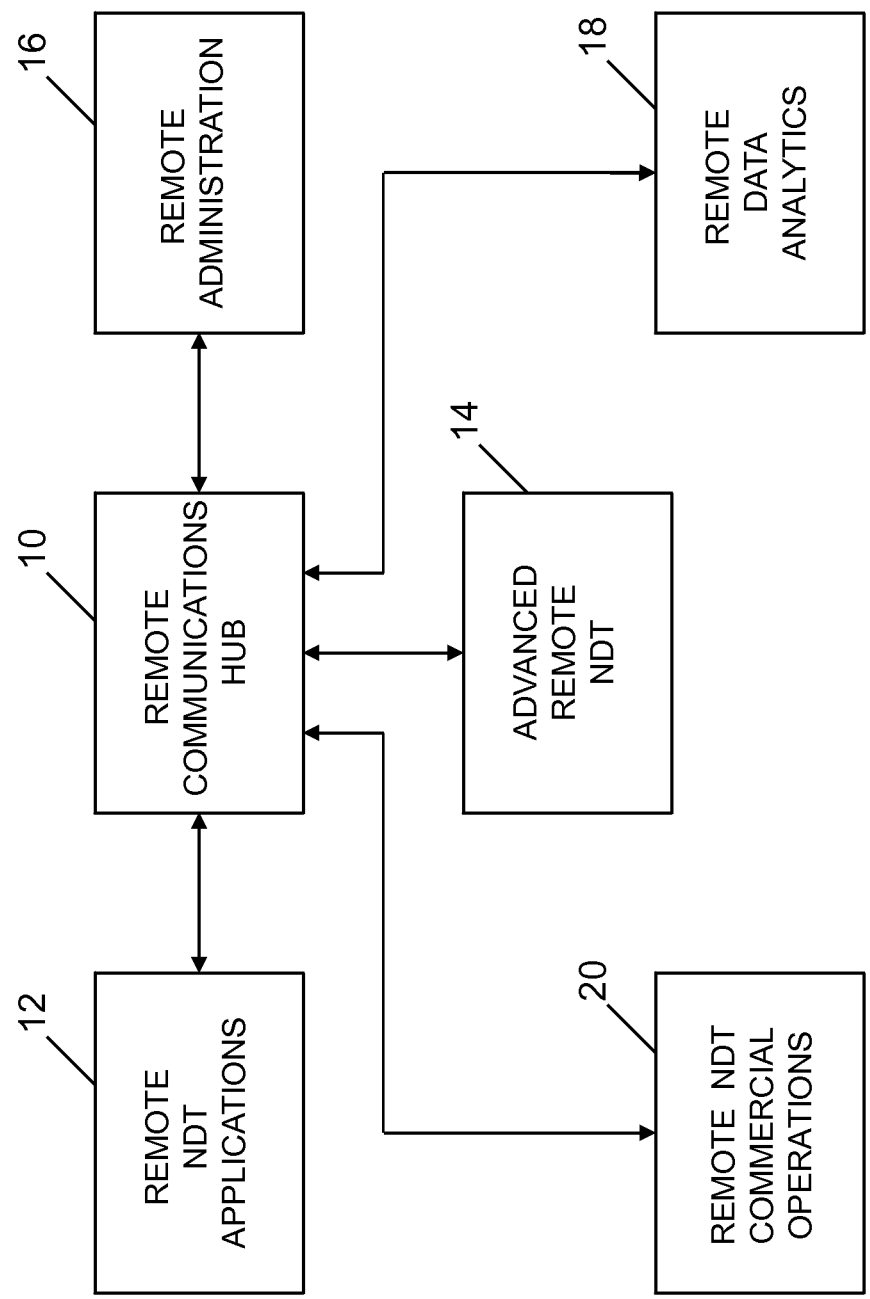
FIG. 1 is a block diagram identifying networked elements of a remote expert NDT system that has a remote communications hub.

A remote NDT system saves time in cases of unplanned maintenance, particularly when the aircraft is grounded in a remote location. One embodiment of a remote NDT system will now be described for the purpose of illustration.

In accordance with one embodiment, a system is provided that extends remote expert NDT methodology to a variety of manufacturing and in-service processes. The elements of such a system are identified in FIG. 1. The system comprises a remote communications hub 10 that can communicate with other system elements. Those system elements may comprise remote NDT applications 12, advanced remote NDT 14, a remote administration system 16, a remote NDT commercial operations center 20, and a remote data analytics system 18. All of the remote NDT applications 12, advanced remote NDT 14, remote administration system 16, remote NDT commercial operations center 20, and remote data analytics system 18 are networked for data transfer to and from the remote communications hub 10. Those data communication links are indicated by double-headed arrows in FIG. 1. Each arrow may represent a multiplicity of communication links. For example, the remote communications hub 10 may comprise multiple computer systems (referred to hereinafter as "remote workstations") which can communicate with multiple geographically distributed computer systems running the remote NDT applications 12.

Figure 2:
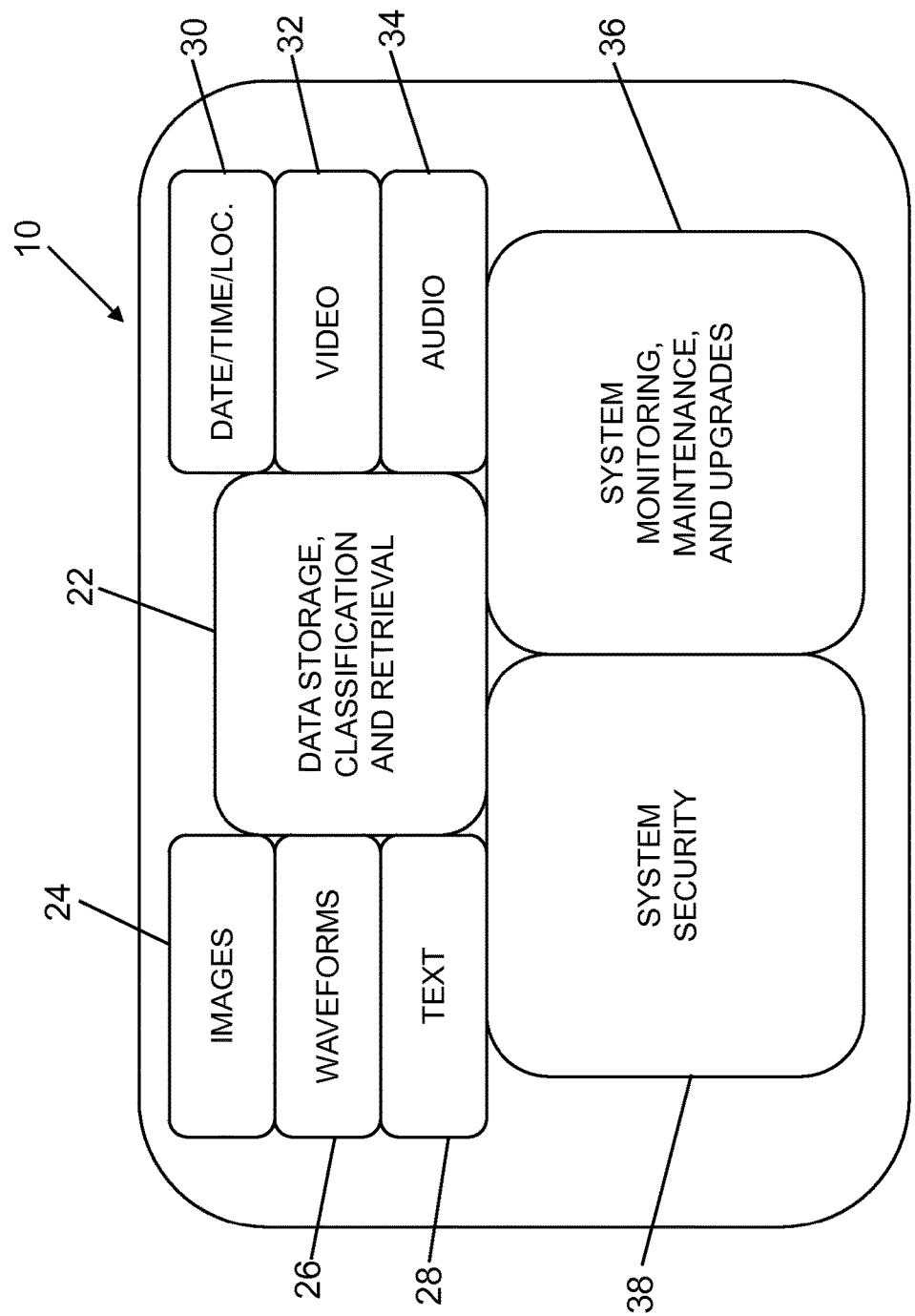
FIG. 2 is a diagram identifying categories of functions performed by the remote communications hub of the remote expert NDT system diagrammed in FIG. 1.

FIG. 2 is a diagram identifying categories of functions performed by the remote communications hub 10 of the remote expert NDT system diagrammed in FIG. 1. The remote communications hub 10 enables the storage, classification, and retrieval 22 of data, which includes images 24, waveforms 26, text 28, date/time/location/inspector/system/ etc. records 30, video 32, and audio 34. It also serves as the interface for system monitoring, maintenance, and upgrades 36 and system security 38. The remote communications hub 10 may include multiple computer systems for performing one or more of the aforementioned functions (i.e., data storage, data classification, data retrieval, system monitoring, system maintenance, system upgrade, and system security). The system monitoring function may include monitoring how much memory has been used, how many communications have occurred on each channel, when do system components need to be upgraded, and so forth. The system security function may include receiving identification data from potential system users and verifying that the potential system users are authorized users.

Figure 2A:
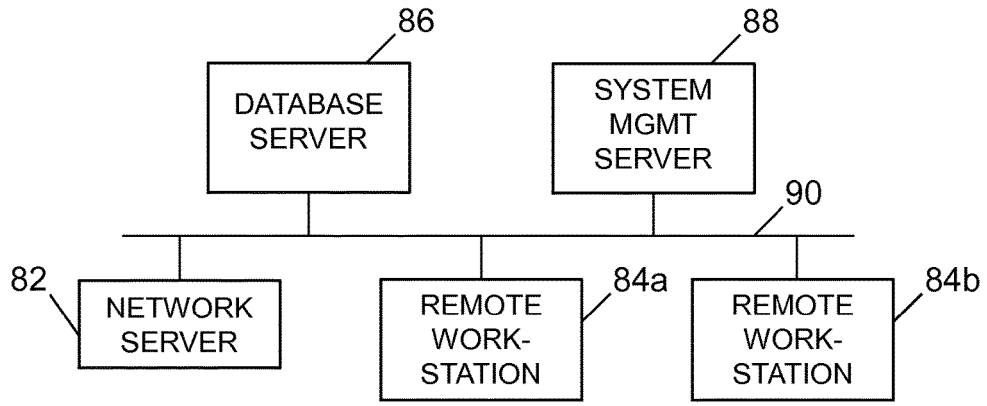
FIG. 2A is a block diagram identifying components of a remote communications hub in which computers communicate via a local area network.
Figure 2B:
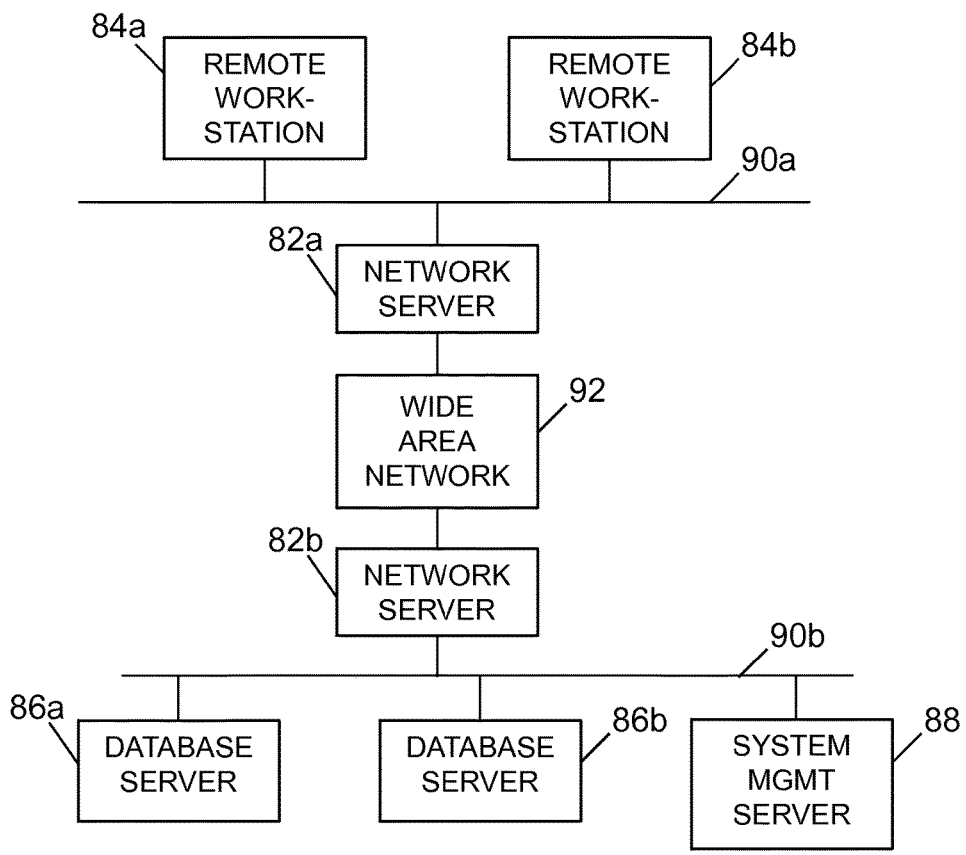
FIG. 2B is a block diagram identifying components of a remote communications hub in which some computers communicate via a wide area network.

In accordance with one embodiment, the remote communications hub 10 may comprise a single computer. In other embodiments, the remote communications hub 10 comprises a multiplicity of computers which are interconnected by a network. The network may have any one of a plurality of suitable architectures. For example, in the architecture depicted in FIG. 2A, a network server 82, remote workstations 84a and 84b, a database server 86, and a system management server 88 are interconnected by a local area network 90. Ethernet over twisted pair cabling and Wi-Fi are the two most common technologies currently used to build local area networks. In one implementation, the components identified in FIG. 2A may be housed in one building. In accordance with an alternative architecture depicted in FIG. 2B, a network server 82a and remote workstations 84a and 84b are interconnected by a local area network 90a; a network server 82b, database servers 86a and 86b, and a system management server 88 are interconnected by a local area network 90b; and network servers 82a and 82b can communicate via a wide area network 92 (e.g., the Internet). In another implementation, the components identified in FIG. 2B may be housed in different buildings. Many other networking architectures are possible.

As used herein, the term "database server" refers to a computer that runs a computer program that provides database services to other computer programs or computer systems. As used herein, the term "network server" refers to a computer that runs a computer program that provides networking services to other computer programs or computer systems.

Figure 3:
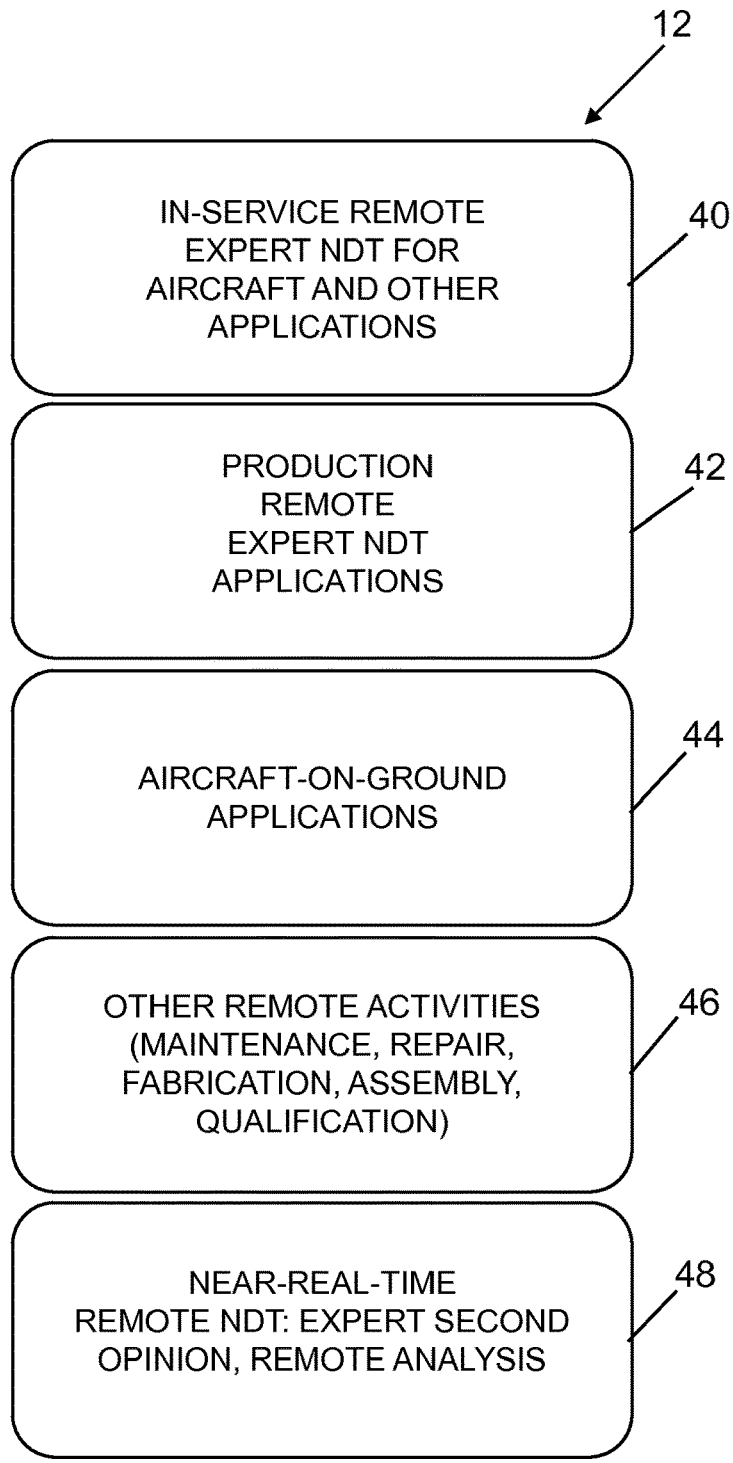
FIG. 3 is a diagram identifying categories of remote NDT applications of the remote expert NDT system diagrammed in FIG. 1.

FIG. 3 is a diagram identifying categories of remote NDT applications 12 of the remote expert NDT system diagrammed in FIG. 1. The remote NDT applications 12 are the NDT applications which can be run at a multiplicity of geographically distributed inspection sites. In the embodiment depicted at a high level in FIG. 3, the remote NDT applications 12 comprise in-service remote expert NDT methods 40 (such as the method disclosed in U.S. Pat. No. 8,255,170), production remote expert NDT applications 42, aircraft-on-ground applications 44, other remote activities 46 (such as maintenance, repair, fabrication, assembly, and qualification), and near-real-time remote NDT 48 (such as expert second opinion, remote analysis), which each comprise respective computer systems networked to the system through the remote communications hub 10. This enables software updates to be pushed to the remote tools, and data to be transferred and stored in the remote communications hub 10. The other elements of the remote expert NOT system are accessed through the remote communications hub 10, enabling, in particular, remote administration and analytics of all data collected using the remote NDT applications 12.

Figure 4:
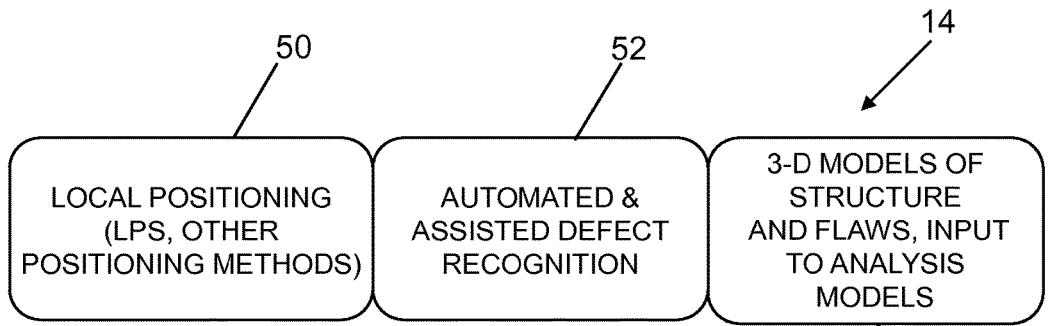

FIG. 4 is a diagram identifying categories of advanced remote NDT 14 which may be included in the remote expert NDT system diagrammed in FIG. 1. In accordance with one embodiment, advanced remote NDT 14 comprises testing, inspection, maintenance, and repair that requires precise locating of the activity relative to the structure being inspected. It enables automated and semi-automated NDT activities and utilizes representative models for improved damage and repair assessments. Advanced remote NDT 14 may comprise local positioning 50 (such as the local positioning system disclosed in U.S. Published Patent Application No. 2012/0327187), automated and assisted defect recognition 52 (comprising computer-executable instructions for processing inspection data to detect and identify defects), and modeling 54 comprising three-dimensional (3-D) models of the structure and flaws, and input to analysis models for performance prediction. The models may comprise respective software modules hosted on one or more computers. For example, a model of a detected flaw can be virtually embedded in a model of the structure and then that virtual flawed structure can be subjected to virtual stresses or loads. The response of the flawed structure to the stresses is then simulated and that simulated response is then compared to a threshold below which the simulated response is acceptable and above which it is unacceptable. The simulated response allows the system to predict the performance of the actual flawed structure. All data generated by the local positioning 50, automated and assisted defect recognition 52, and modeling 54 functionalities can be sent from the respective computers performing those functions to the remote communications hub 10 for storage and classification. In addition, the remote communications hub 10 can retrieve the stored data acquired by advanced remote NDT 14 and send it to the other elements of the remote expert system.

Figure 5:
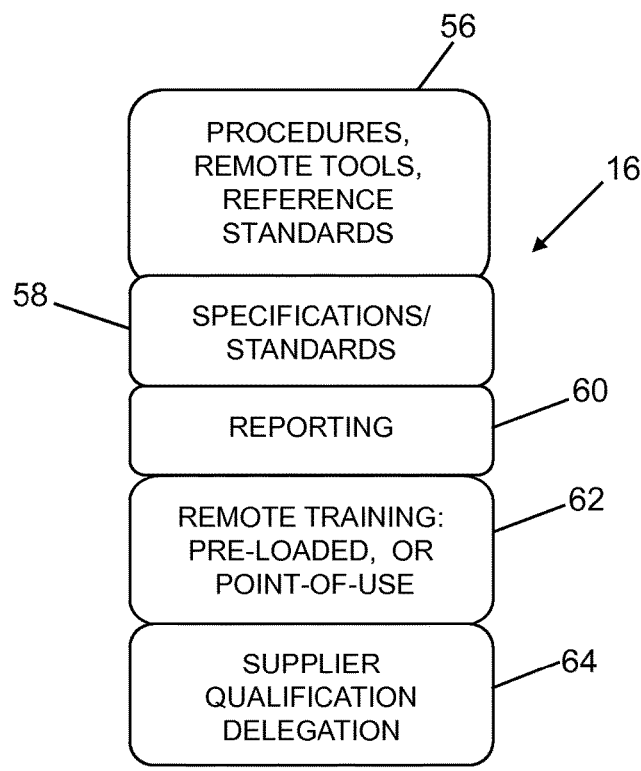
FIG. 5 is a diagram identifying categories of digital representations contained in a remote administration element of the remote expert NDT system diagrammed in FIG. 1.

FIG. 5 is a diagram identifying categories of digital representations which may be included in the remote administration system 16 of the remote expert NDT system diagrammed in FIG. 1. In accordance with one embodiment, the remote administration system 16 comprises one or more computers which contain digital representations 56 of procedures, remote tools, and reference standards (e.g., information for calibrating equipment), digital representations 58 of specifications and standards, digital representations 60 of reporting, digital representations 62 of training, and digital representations 64 related to supplier qualification delegation. Hardware, such as reference standards, and NDT equipment are given tracking information for maintenance, replacement, and upgrades. The training information may comprise instructions and settings pre-loaded on a tool or provided at a point of use as disclosed in U.S. Patent Application Publ. No. 2008/0301152. The other elements of the remote expert system are accessed through the remote communications hub 10, enabling, in particular, data transfer to and from remote NDT commercial operations center 20 and remote data analytics system 18 (see FIG. 1).

FIG. 6 is a diagram identifying categories of functions performed by the remote data analytics system 18 of the remote expert NDT system diagrammed in FIG. 1. The remote data analytics system 18 of the networked remote expert NDT system may comprise one or more computers programmed to receive data stored in the remote communications hub 10 and collected from the remote NDT applications 12, advanced remote NDT 14, and the remote NDT commercial operations center 20. The remote data analytics system 18 comprises one or more computers 66 which run various programs for performing statistical analysis of the acquired data. In accordance with one embodiment, respective computers 66 may host a performance ratings software module 68, a prediction of future events software module 70, a trending software module 72, and a metrics software module 74, all of which involve computer calculations. In particular, the performance ratings software module 68 may comprise data mining software for assessing and rating individuals and companies that do inspections or other maintenance activities. In addition, public disclosure can be done for results that pertain to the public interest, such as safety information. For example, service bulletins can be constructed and then transmitted over a network to portable communications devices as disclosed in U.S. Pat. No. 8,291, 043. In addition, in response to the receipt of data (via the remote communications hub 10) acquired at the location of an aircraft under visual inspection, the remote data analytics system 18 is capable of performing statistical analysis of the data and constructing a report indicating whether the aircraft can fly or is in need of repair, which report is then transmitted to personnel at the location, as disclosed in U.S. Pat. No. 8,825,498.

FIG. 7 is a diagram identifying categories of commercial services available from a remote NDT commercial operations center 20 of the remote expert NDT system diagrammed in FIG. 1. The remote NDT commercial operations center 20 provides commercial services related to the remote expert NDT system. An autonomous support system 76 (comprising mobile platforms and computers for controlling the platforms) provides services such as remote mobile visual capability (i.e., flying, crawling, swimming, swarming, etc. platforms) and remote mobile tool delivery (i.e., a special tool is ordered and delivered via a drone or robot). A remote tracking system 78 provides GPS-enabled locating of an expert who can be called and tied in (i.e., connected to a communications channel) to equipment at an inspection or repair site. The remote tracking system 78 also uses GPS or RFID to enable a tool's location to be determined, so that the tool can be transported to an inspection or repair site quickly. A commercial applications system 80 includes a network of computers for processing data relating to leasing or selling remotely enabled tools, systems, or services. The remote NDT commercial operations center 20 has two-way access to the other elements of the remote expert system through the remote communications hub 10.

The remote expert NDT system disclosed above can be used to provide multifarious NDT services in connection with structural components located at a multiplicity of sites geographically distributed over a wide area. In accordance with one embodiment, suspected damage to a structural component (such as a fuselage or wing of an aircraft) may require more extensive inspection beyond visual observation or simple measurements. For example, a computer-controlled non-destructive inspection device at the inspection site may be linked to the remote communications hub, where the inspection data may be received for interpretation by an NDT expert.

As used herein, the term "computer system" should be construed broadly to encompass a system having at least one computer or processor, and which may have multiple computers or processors that communicate through a network or bus. As used in the preceding sentence, the terms "computer" and "processor" both refer to devices comprising a processing unit (e.g., a central processing unit, an integrated circuit or an arithmetic logic unit), a memory and a bus connecting the processing unit and the memory.

In summary, the remote expert non-destructive testing system depicted in FIG. 1 comprises a remote communications hub 10 and a multiplicity of non-destructive testing equipment (used in remote NDT applications 12) located at respective testing sites and networked to the remote communications hub 10 by respective communication links. The remote communications hub 10 comprises a multiplicity of computers and a network interconnecting the multiplicity of computers. In addition, the remote communications hub 10 comprises a security system (see system security 38 in FIG. 2) configured to limit access to the system. The remote communications hub 10 comprises one or more databases storing non-destructive testing data acquired by the multiplicity of non-destructive testing equipment. The system may further comprise a local positioning system networked to the remote communications hub 10 (see LPS hardware 510 and LPS controller 512 networked to remote workstation 530 in FIG. 10). The remote expert non-destructive testing system may further comprise a computer system networked to the remote communications hub, which computer system is programmed to perform one of a multiplicity of functions, such as: defect recognition based on non-destructive testing data received from the remote communications hub 10; modeling of structures and flaws in three-dimensional space based on non-destructive testing data received from the remote communications hub 10; analysis of non-destructive testing data received from the remote communications hub 10; determining a location of an expert or tool and sending expert or tool location information to the remote communications hub 10; tracking a mobile platform and sending mobile platform location information to the remote communications hub 10; and sending procedures, specifications, standards, reports and training to the remote communications hub 10 in response to requests from the remote communications hub 10.

In accordance with some embodiments, the method for operating the remote expert non-destructive testing system comprises: sending guidance from a remote communications hub to an inspection site; performing non-destructive testing of a structure using non-destructive testing equipment located at the inspection site in accordance with the guidance; sending non-destructive testing data acquired during the non-destructive testing from the inspection site to the remote communications hub; storing the non-destructive testing data at the remote communications hub; sending the non-destructive testing data from the remote communications hub to a first computer system programmed to process non-destructive testing data; and processing the non-destructive testing data using a computer program hosted on the first computer system. The processing may comprise one or more of the following: recognizing defects based on the non-destructive testing data received from the remote communications hub; modeling structures and flaws in three-dimensional space based on the non-destructive testing data received from the remote communications hub; or analyzing the non-destructive testing data received from the remote communications hub. The method may further comprise: storing digital representations of procedures, specifications, standards, and training instructions in a database at a location that is not part of the remote communications hub; and sending a digital representation from the database to the remote communications hub in response to a request from the remote communications hub, wherein the guidance comprises the digital representation received by the remote communications hub. In addition or in the alternative, the method may further comprise: sending equipment location data from the inspection site to a second computer system programmed to track locations of equipment; and tracking locations of equipment using a computer program hosted on the second computer system; and sending equipment location information from the second computer system to the remote communications hub in response to a request from the remote communications hub. In addition or in the alternative, the method may further comprise: monitoring states of the non-destructive testing equipment located at the inspection site; and uploading a software upgrade to equipment at the inspection when the monitoring indicates that an upgrade is due.

For the purposes of this disclosure, the term "remote location" refers to the location of a communications hub capable of communicating with multiple sites where structural components under inspection are located. In this situation, the "remote location" may be viewed as being centrally located relative to a multiplicity of sites. Nevertheless, such a "centrally located" communications hub will be described herein as being at a remote location, not a central location. In addition, it should be appreciated that the remote location and the inspection site can be separated by any distance. Also, the NDT expert may be a skilled, certified, or licensed NDT technician competent to provide an NDT data evaluation that may include technical analysis of the inspection data and a recommendation in the form of a repair disposition decision which is a function of the results of the technical analysis.

The repair disposition decision may include a decision to dispatch the aircraft, order a quick composite repair, or take the aircraft out of service for permanent repair, which may be routed back through the communications link or channel to the personnel at the NDT device. That is, personnel at the aircraft or at the boarding area. The link between the NDT device and the network can be a physical network connection, but it may be preferable to employ wireless network communications to take advantage, for example, of the possible portability of the NDT device.

Figure 8:
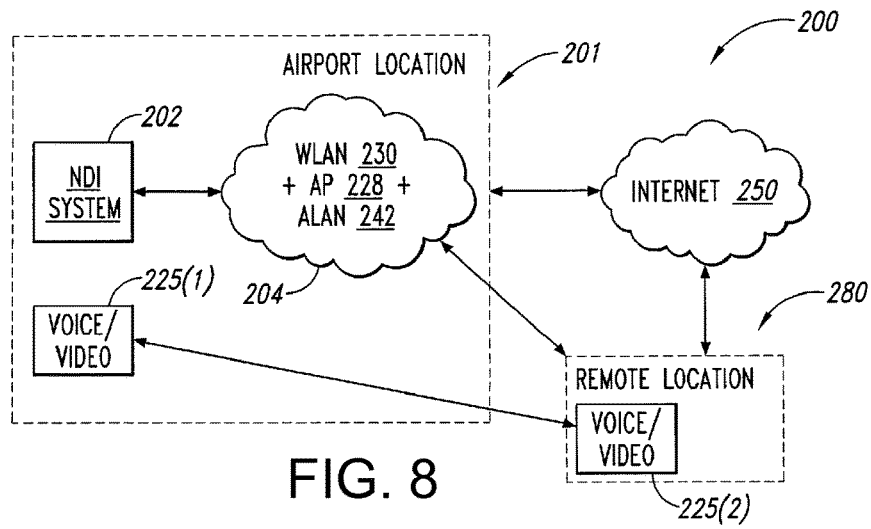
FIG. 8 is a diagram depicting the configuration of a remote non-destructive inspection system for an aircraft-on-ground application in accordance with one embodiment.

FIG. 8 shows an inspection system 200 in accordance with one embodiment of an aircraft-on-ground application (see aircraft-on-ground applications 44 in FIG. 3). Inspection system 200 includes an airport location 201 and a remote location 280 (i.e., the location of a remote workstation that is part of a remote communications hub) at some distance from the airport location. These locations may be linked by a network, such as a network 204 and/or the Internet 250. For example, airport location 201 may include one or more non-destructive inspection (NDI) systems 202, which link to Internet 250 via an access point 228, a wireless local area network (WLAN) 230, and/or an airport local area network (ALAN) 242. Other network types and/or topologies may be used.

Inspection system 200 may further include voice and/or video camera communications over a separate audio/video communications link 225(1), 225(2) between airport location 201 and remote location 280 to facilitate operation of NDI system 202 under the direction of personnel at remote location 280. For example, a mobile phone (e.g., voice) and video camera may be used to aid the placement and operation of NDI system 202. The audio/video communications link 225(1), 225(2) may be provided through the same network 204 used by NDI system 202 or may utilize a different network.

Figure 9:
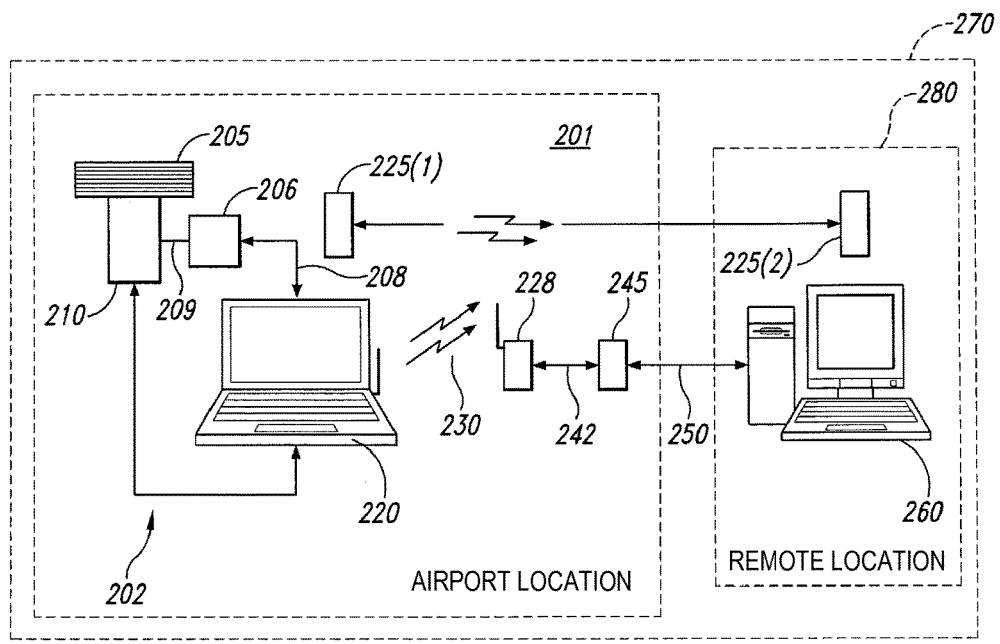
FIG. 9 is a diagram identifying components of the remote non-destructive inspection system depicted at a high level in FIG. 8.

FIG. 9 shows an inspection system 270 in accordance with another embodiment, which may represent an example of specific implementation details of inspection system 200. For example, NDI system 202 may include one or more of an NDI device 210 coupled to a local computer 220, or local computer system (e.g., an on-site PC controller). Alternatively, the separate functions of NDI device 210 and local computer 220 may be combined into a single integrated NDI system 202 with the functional capabilities of both NDI device 210 and local computer 220, including communications (e.g., wireless communications) as described herein.

Still referring to FIG. 9, a section of an aircraft composite structure 205 may be inspected using NDI device 210. NDI device 210 may be capable of producing inspection data, such as images or other forms of data regarding surface and subsurface features of composite structure 205, including internal structure and delamination or cracking damage corresponding to a damage condition of the inspected structure at a damage site. As an example, local computer 220 may be capable of receiving image data from NDI device 210, displaying the images, and/or storing the image data on a computer-readable medium, which may be an internal or external component of local computer 220. Local computer 220 may also be capable of controlling NDI device 210 with suitable software, depending upon the application.

Local computer 220 may be equipped to transmit the data (e.g., image data) over WLAN 230 to ALAN 242 through access point 228 (e.g., a WLAN/ALAN gateway access node). ALAN 242 may be connected via an ALAN/Internet gateway node 245 to the Internet 250. The network link to NDI system 202 may be a wireless network (e.g., WLAN 230) for this example. However, other embodiments that employ hard-wired network connections (e.g., Ethernet) may also be used.

Data from NDI system 202 may be transmitted via the Internet 250 (or a dedicated communications link) to a remote workstation 260 at a remote location 280 which is part of the remote communications hub 10 seen in FIG. 1. An NDT expert may perform detailed inspection and evaluation at such a remote workstation 260. Remote location 280 may, for example, be a site operated by an aircraft manufacturer, an OEM manufacturer of the aircraft component being inspected, an operations/repair facility of an airline company, or a third-party service company located on-airport or off-airport.

While communication of inspection data may take place via a data network (e.g., network 204 in FIG. 8), voice (e.g., telephony) and/or video communication may also occur over this network or a separate communication link (e.g., cellular). For example, the on-site personnel may be in communication from audio/video communication link 225(1) with personnel at remote location 280 at audio/video communication link 225(2) (e.g., a phone, s-video, or s-video conference link). Alternatively, portions of audio/video communication may also take place via data and voice transmitted via network 204 and/or the Internet 250.

The inspection system 270 depicted in FIG. 9 may include a robotic device 206, or robotic system, capable of direct manipulation 209 of NDI device 210 via commands originating from the local computer 220, via communications channel 208. Control of robotic device 206 may result from automated procedures included in a computer program operating on local computer 220 or, alternatively, from commands provided by the NDT technician at local computer 220 using, for example, keyboard commands or a joystick controller (not shown). Alternatively, control of robotic device 206 may result from similar commands originating from remote workstation 260 at remote location 280, under the control of automated procedures included in a computer program or, alternatively, from commands provided by the skilled NDT expert at remote workstation 260 using, for example, keyboard commands or a joystick controller (not shown).

In addition to providing guidance during non-destructive inspection, an expert situated at a remote workstation of the remote communications hub 10 (see FIG. 1) may also observe and provide guidance during a repair procedure at a local site. In some cases, it may be advantageous for the expert to arrange for the projection of repair guidance images onto the structure being repaired for use by the technician performing the repair procedure. For example, U.S. patent application Ser. No. 14/719,141 (the disclosure of which is incorporated by reference herein in its entirety) discloses systems and processes for enabling an off-site expert to interact with an on-site technician during repair of composite structure. The off-site expert can provide real-time guidance to an on-site technician before and during the performance of repair procedures to avoid errors. The off-site expert is also able to monitor the repair procedures in real time to verify that correct procedures are being employed. In particular, the systems and processes disclosed in U.S. patent application Ser. No. 14/719,141 can provide direct visual guidance, feedback, and out-of-plan warnings for manual or automated scarfing and other operations during repair of composite structure. In some embodiments, the repair process combines optical 3-D surface measurement, illumination by at least one of visible, ultraviolet and infrared light, and digital light processing projection to provide step-by-step monitoring of the repair by a remotely located repair expert.

Figure 10:
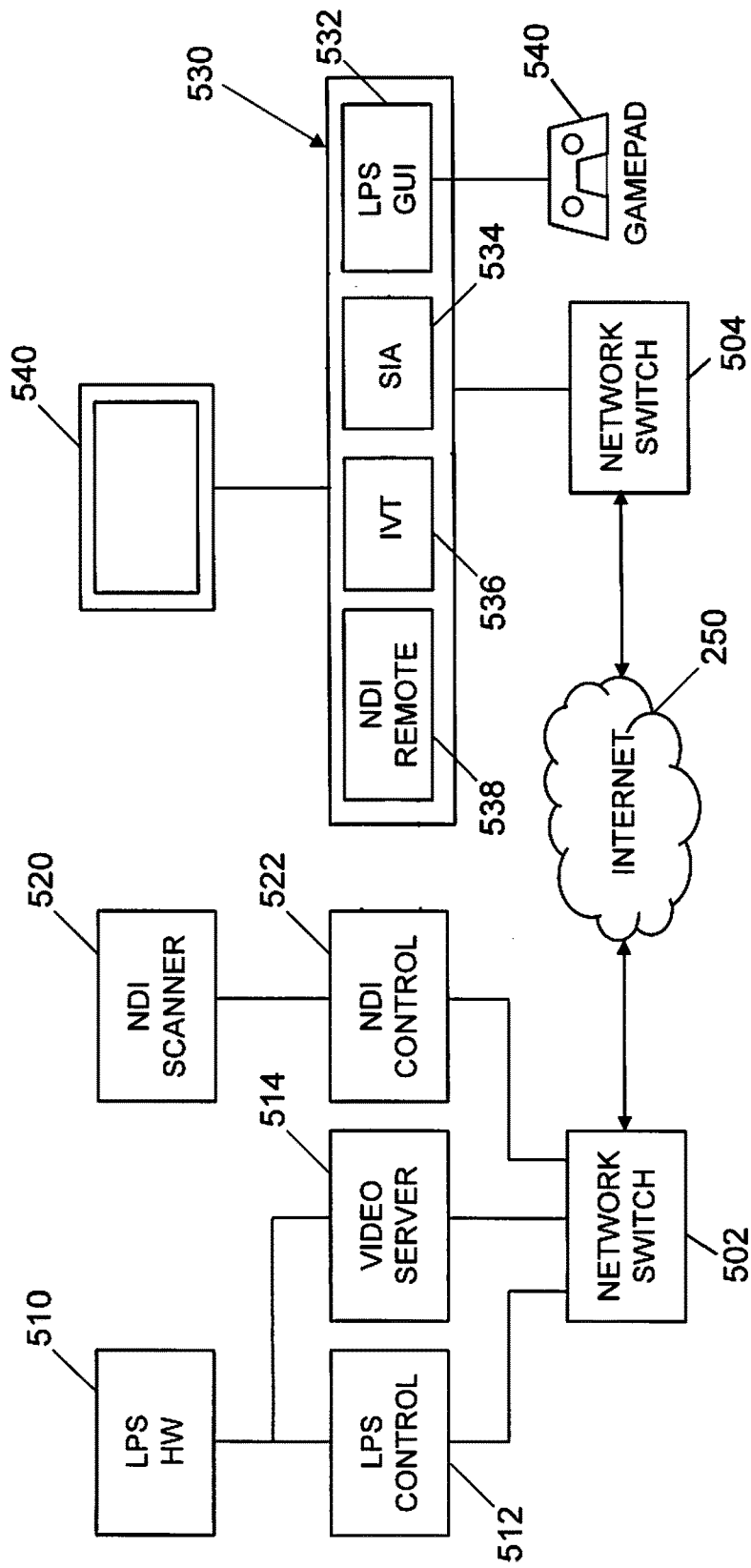
FIG. 10 is a block diagram identifying components of a remote non-destructive inspection system for an aircraft-on-ground application in accordance with an alternative embodiment that employs a local positioning system.

FIG. 10 is a block diagram identifying components of a remote non-destructive inspection system for an aircraft-on-ground application in accordance with an alternative embodiment that employs a local positioning system. This remote acquisition and analysis system for non-destructive inspection employs multiple hardware and software components networked through a central analysis interface. The integration of these components enables a remote operator to acquire and analyze inspection data using automated scanning equipment and a local positioning system (LPS), and then visualize and interact with the data in 2-D and 3-D analysis software. Alignment points measured by the LPS in the scanning area are used to create a positional correspondence for setup of the scanning equipment and registering the resulting 2-D scan data in the coordinate system of a 3-D CAD model visualization environment as disclosed in detail in U.S. Patent Application Publ. No. 2012/0327187, the disclosure of which is incorporated by reference herein in its entirety.

The ability to operate all of the hardware and software components remotely enables data collection by an expert NOT analyst situated at the remote communications hub, with the only on-site assistance coming from non-expert support personnel to setup the LPS and NDI scanning hardware.

The primary on-site and off-site hardware components can be interconnected as shown in FIG. 10. The LPS hardware 510 and an NDI scanner 520 are located at the site where the article to be inspected (e.g., an aircraft 14. The remote workstation 530 with master display 540 is a component of the remote communications hub and is located at a distance from the inspection site. An NDT expert seated at the remote workstation 530 can remotely control both the LPS hardware 510 and the NDI scanner 520.

The LPS hardware 510 can be used to determine local 3-D coordinates of the aircraft. The LPS may comprise an LPS controller 512, typically a personal computer (PC). The LPS hardware 510 comprises a servo-controlled video, distance measurement, and pointing system having a video camera mounted to a pan-tilt unit and incorporating a laser pointer. One such LPS is disclosed in U.S. Pat. No. 7,859,655, the disclosure of which is incorporated by reference herein in its entirety. The video camera is connected to a video server 514.

The NDI scanner 520 may comprise a Mobile Automated Ultrasonic Scanner (MAUS®), which comprises a scanning unit having a support rail mountable to the aircraft fuselage and a translation rail supporting an ultrasonic probe. The translation rail moves along the support rail for a first axis of scan as the probe moves along the translation rail for a second orthogonal axis of scan. The NDT scanner 520 is controlled by an NDI controller 522, which again may be a PC controller.

As depicted in FIG. 10, the on-site LPS controller 512, video server 514 and NDI controller 522 may communicate with the remote workstation 530 via a first network switch 502, the Internet 250, and a second network switch 504. For conducting an inspection operation, some of the initial tasks performed by the technician at the inspection site include: setting up the equipment depicted in FIG. 10 and connecting that equipment to the network switch 502. After setup, the video camera allows an NDT expert at the remote workstation 530 to help guide the rest of the process.

When the on-site setup of the LPS is complete, the NDT expert at the remote workstation 530 can connect to the LPS controller 512 through a network socket connection (not shown in FIG. 10) in the remote workstation 530 to operate the LPS pan-tilt unit, camera, and laser range meter/laser pointer using a LPS graphical user interface (GUI) 532 and a manual controller 540 (e.g., a gamepad). The visual display of the LPS GUI 532 and associated video from the video server 514 can be displayed on the master display 540. The LPS GUI 532 allows communication from the LPS controller 512 of location data and video data from the video server 514 to the remote workstation 530 and control of the LPS hardware 510 from the remote workstation 530.

Once the remote connection has been established, the LPS can be used to communicate with the on-site support technician to help guide the setup of the NDI scanner 520. The NDT expert can direct the on-site support technician to place the NDI scanner 520 in the proper position on the aircraft using the LPS laser pointer while viewing the operation via the LPS camera (along with an audio channel provided by a microphone built into the camera unit, cell phones or similar devices or a land-line telephone).

Once the NDI scanner 520 has been properly positioned and the NDI controller 522 has been setup and connected to the network switch 502, the on-site support technician is directed to place three fiducial markers on the aircraft fuselage within the scan region. The NDT expert can point out these locations using the LPS laser pointer remotely controlled through the LPS GUI 532 and manual controller 540. The NDT expert can then direct a calibration process to enable registration of the scan images to the aircraft coordinate system. More specifically, using information from a CAD database, at least three fiducial markers (i.e., optical targets) can be attached to the surface of the fuselage at known locations around an area that requires inspection. For example, a fiducial marker could be located at certain distances from a pair of structural features having known coordinates in the frame of reference of the fuselage. Three fiducial markers attached to a fuselage can be used to register an acquired image of the inspected area to the actual structure of the fuselage. The absolute position (in the fuselage coordinate system) of the fiducial markers attached to a fuselage can be verified using the LPS, which can measure the actual distances between each fiducial marker and the camera, thereby enabling a determination of the correct 3-D locations of the set of three fiducial markers within the fuselage coordinate system.

The NDI scanner 520 can be connected via the Internet 250 to an NDI remote desktop display application 538, such as Windows Remote Desktop Connection, which interfaces to the NDI controller 522. A Scan Integration Application (SIA) software module 534 allows communication of NDI scan data to the remote workstation 530 and control of the NDI scanner 520 from the remote workstation 530. The NDT expert can set the scanning software parameters and begin the scan. During a scanning operation, 2-D NDI scan data is acquired and sent from the NDI controller 522 to the remote workstation 530 for display as a scan image on the master display 540. A connection to a 3-D CAD model visualization application such as an Integration Visualization Tool (IVT) 536 is provided through a network socket connection through a plug-in interface that can send and receive object location data, virtual camera location data, and selection point positions. The SIA software module 534 can then provide 3-D coordinates to the 3-D IVT 536 to align the virtual camera with the proper target coordinates, so that a presented 3-D view in a 3-D visualization display field on the master display 540 is perpendicular to the surface at the scan location.

Following completion of the scanning operation, the NDT expert at the remote workstation 530 can analyze the inspection data and make a decision whether the aircraft is in condition to fly or should be taken out of service for repair. That decision may be communicated to personnel at the inspection site in the form of a service bulletin.

Systems and methods for enabling the distribution of service bulletins to portable communication devices by a remote system are disclosed in U.S. Pat. No. 8,291,043, the disclosure of which is incorporated by reference herein in its entirety. In various implementations, the remote system (e.g., remote communications hub 10 in FIG. 1) comprises a server, and the portable communication device (e.g., located at an inspection site) comprises a cell phone or personal digital assistant. The portable communication device includes the following: a display component that displays the service bulletin data for viewing by the user; a user input component that receives input from the user including the registry number of the aircraft; and a portable database component for storage of service bulletin data related to the aircraft.

Figure 11:
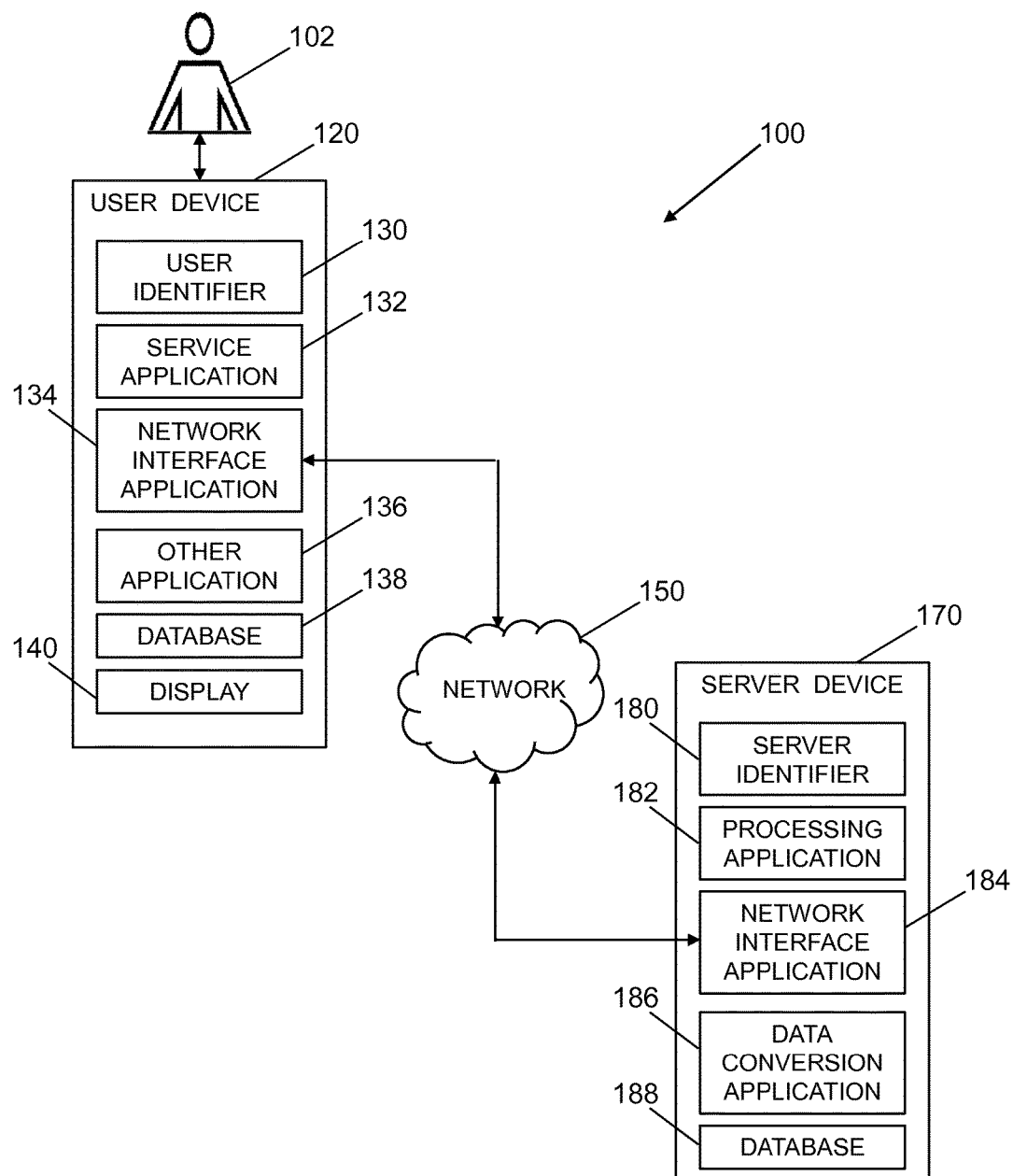
FIG. 11 is a block diagram identifying components of a system configured to transfer service data and information over a network in accordance with one embodiment.

FIG. 11 is a block diagram identifying components of a system 100 (e.g., an interactive communications system) to facilitate the transfer of service data and information over a network 150 in accordance with one embodiment. For example, a decision by an NDT expert at a remote communications hub regarding the state of an aircraft can be communicated to a user 102 located at the inspection site. As shown in FIG. 11, the system 100 includes at least one user device 120 configured to interface with a user 102 and at least one server device 170 configured to communicate with the user device 120 via the network 150.

In accordance with one embodiment, the network 150 may be implemented as a single network or a combination of multiple networks. For example, in one embodiment, the network 150 may comprise a wireless telecommunications network (e.g., cellular phone network) adapted to communicate with other communication networks, such as the Internet. In various other embodiments, the network 150 may include the Internet and/or one or more intranets, landline networks, wireless networks, and/or other appropriate types of communication networks adapted to communicate with a wireless telecommunications network.

The user device 120 may comprise a mobile communication device, such as an ultra-portable communication device (e.g., a cell phone, a personal digital assistant, or some other generally known type of portable communication device). The user device 120 may be implemented using any appropriate combination of hardware and/or software configured for wired and/or wireless communication over the network 150.

In accordance with one embodiment, the user device 120 comprises a user identifier 130, which may be implemented as an operating system registry entry, an identifier associated with hardware of the user device 120, or various other appropriate identifiers. The user identifier 130 may include attributes related to the user 102, such as security information (e.g., user name, password, photograph image, biometric id, address, phone number, etc.). In various implementations, the user identifier 130 may be passed with a user service request to the server device 170, and the user identifier 130 may be used by the server device 170 to provide the user 102 with access to service data and information stored by the server device 170, in a manner as described herein.

The user device 120 may further comprise a service application 132 that enables the user 102 to access and/or browse service data and information made available to the user 102 by the server device 170 over the network 150. For example, the service application 132 may be implemented as a network browser to display service data and information (e.g., documents and/or files related to an advisory service bulletin, a service manual or service instructions) provided by the server device 170 over the network 150. The user device 120 further comprises a network interface application 134 that interfaces the user device 120 to the network 150. The user device 120 may include other applications 136 as may be desired in particular embodiments to make additional features available to the user 102. For example, such other applications 136 may include security applications for implementing client-side security features, programmatic client applications for interfacing with appropriate application programming interfaces (APIs) over the network 150 or various other types of generally known programs and/or applications.

In one implementation, the service application 132 processes relevant inspection data and information to provide an interactive process to guide the user 102 through inspection and maintenance activities. The service application 132 may generate one or more records of the responses to tests, recordings, evaluations and/or assessments made by the user 102 and stores the one or more records in a local memory component, such as database 138. The service application 132 may also provide portable access to large information data sets necessary to operate and maintain machinery, such as a commercial airplane. In addition, the service application 132 may index and store specifications and manuals relating to aircraft structure. Service manual data sets may be retrieved from the server device 170, stored locally in database 138, and displayed for viewing on display device 140.

In accordance with one embodiment, the service device 170 (e.g., a remote workstation that is part of a remote communications hub) may be adapted to operate as an interactive data storage facility and communicate with the user device 120 by transmitting and inspection, repair or maintenance data and information over the network 150. In one implementation, the server device 170 may serve as a service bulletin repository for recording service data and information (e.g., documents and/or files related to advisory service bulletins and service manuals) sent to and received from the user device 120. The server device 170 is configured to extract, format and provide relevant service data and information for transmission to and reception from the service application 132 of the user device 120.

The server device 170 may comprise a server identifier 180, which may be implemented, for example, as an operating system registry entry, an identifier associated with hardware of the server device 170, or various other appropriate identifiers that identify the server device 170. In various implementations, the server identifier 180 may be passed with a response to a user request.

The server device 170 may further comprise a processing application 182, a network interface application 184, a data conversion application 186, and one or more databases 188. The network interface application 184 may comprise a network communication device, module and/or application that allows the server device 170 to communicate with the user device 120 via the network 150 to transmit and receive service data and information.

The processing application 182 is adapted to download the service application 132 (e.g., an interactive software application) to the user device 120 (e.g., a portable communication device) over the network 150. The processing application 182 is adapted to interact with the user 102 via the interactive service application 132 to exchange data, such as service bulletin data, with the user device 120 over the network 150.

The data conversion application 186 may comprise a data conversion mechanism or module that allows translation of part identification numbers into user-readable information that may reference maintenance, service and repair procedures from documents and/or files related to advisory service bulletins and/or service manuals stored in a database 188. The database 188 may be adapted to store and archive data and information derived from maintenance documents (e.g., advisory service bulletins and/or service manuals). In one implementation, the user 102 may input into the user device 120 a part number from a particular part of the machinery, such as an aircraft, and access specific topics in the service manual for specific information related to maintenance, service and/or repair procedures for that specific part, which is sent by the server device 170. This allows the user 102 to quickly identify and research the particular part directly in data and information stored locally on the user device 120, such as a cell phone.

Figure 12:
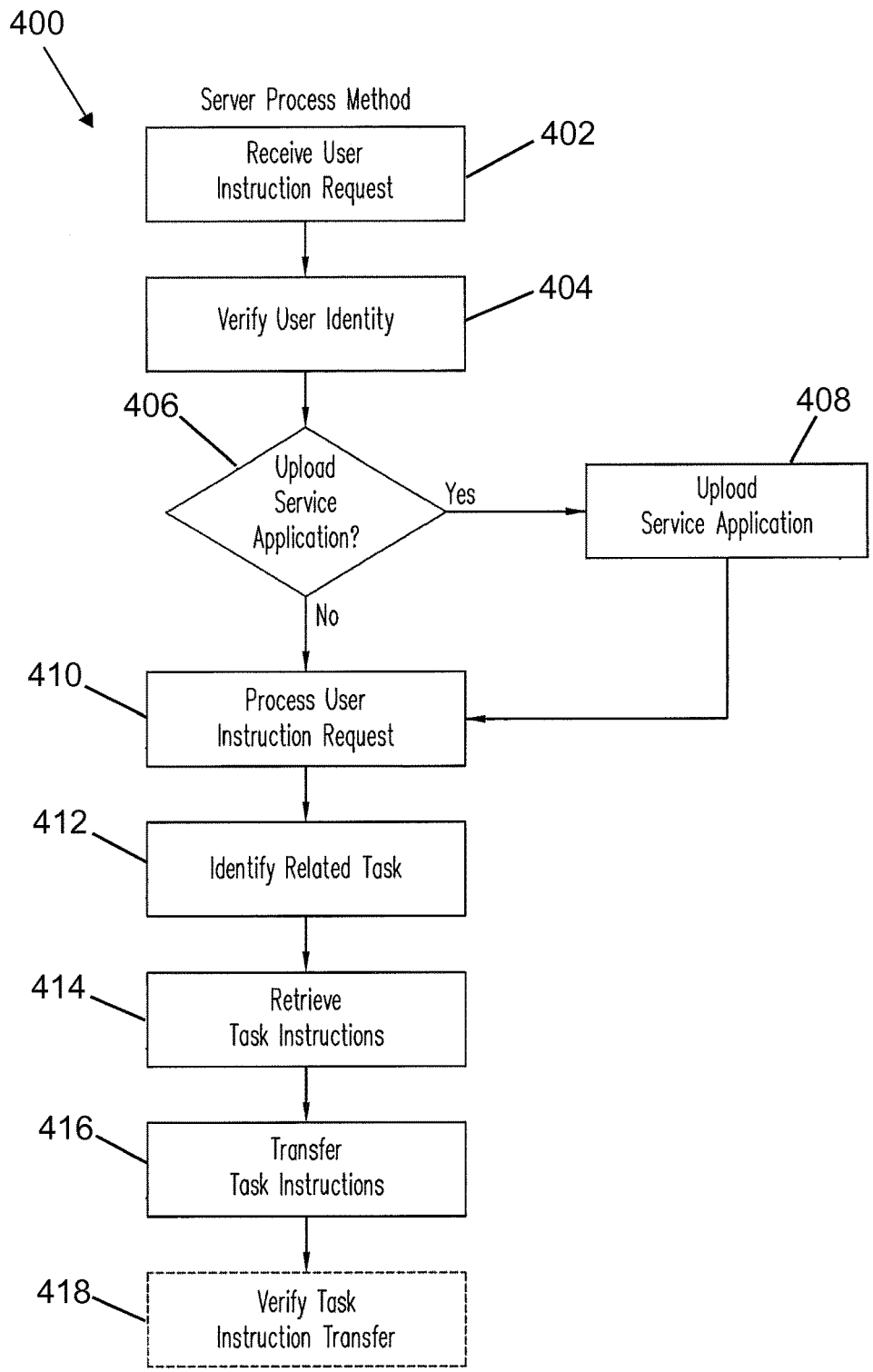
FIG. 12 is a flowchart identifying steps of a server process method for transferring task instruction data and information to a user device via a network in accordance with one embodiment of a point-of-use training system.

As should be apparent from the previous discussions of FIGS. 1, 3 and 5, an NDT expert at the remote communications hub 10 can retrieve training materials from the remote administration system 16 and send those materials to one of the remote NDT applications 12 for point-of-use training of a technician. FIG. 12 is a flowchart identifying steps of a server process method for transferring task instruction data and information to a user device via a network in accordance with one embodiment of a point-of-use training system.

Certain operations on an airplane, though relatively simple, demand skilled workmanship. In many situations (e.g., when an aircraft is at a loading gate), it may not be possible to summon individuals with the needed training to the scene. It such situations, it is desirable that a mechanic be able to quickly access guidance and/or instructions that describe how to properly perform a maintenance or repair operation.

FIG. 12 shows one embodiment of a server process method 400 for transferring task instruction data and information to a portable user device via a network. In one implementation, the server device receives a user instruction request from the user via the user device over the network (step 402). Next, the server device verifies the identity of the user based on information passed with the user instruction request (step 404). Next, the server device determines whether to upload a service application to the user device via the network based on information passed with the user instruction request (step 406). For example, the user may request permission to download the service application as part of the user instruction request. As such, the server device may decide to upload the service application to the user device (step 408) and then process the user instruction request (step 410). Otherwise, if the server device determines that an upload is not necessary, then the server device proceeds with processing the user instruction request (step 410) without uploading a service application. Next, the server device identifies one or more tasks related to the user instruction request based on information passed with the request (step 412) and retrieves one or more task instructions from a database based on information passed with the user instruction request (step 414). For example, the server device may receive information related to a serial number for an aircraft and/or part thereof and then retrieve repair task instructions related to the aircraft and/or part thereof from the database. Next, the server device transfers the retrieved task instructions to the user device via the network (step 416). Next, the server device may optionally verify the transfer of the task instructions to the user device via the network (step 418). In one implementation, verification of transfer may include receiving a response from the user device upon delivery.

Figure 13:
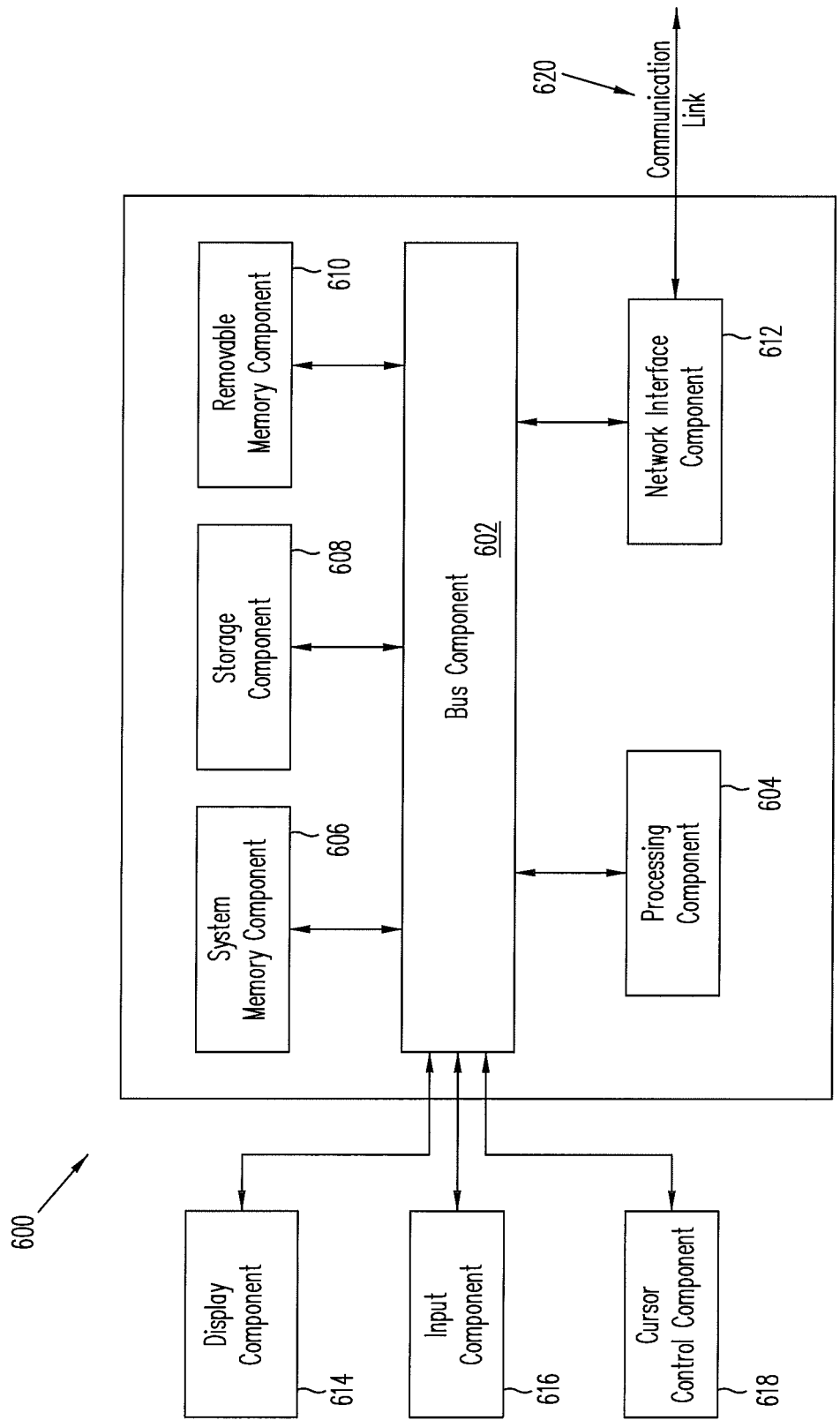
FIG. 13 is a block diagram identifying components of a computer system suitable for use as a remote workstation which is part of the remote communications hub and is configured for communication with a computer system at an NDT site.

FIG. 13 is a block diagram identifying components of a generic computer 600 which can be programmed to perform operations of the types disclosed herein. Any of the various computers of the remote communications hub may comprise the same components identified in FIG. 13. Computer 600 comprises a bus 602 or other communication mechanism for communicating information, which interconnects subsystems and components, such as processor 604, system memory component 606 (e.g., RAM), static storage component 608 (e.g., ROM), removable memory component 610 (e.g., removable ROM memory, such as EEPROM, smart card, flash memory, etc.), wired or wireless communication interface 612 (e.g., transceiver, modem or Ethernet card), display component 614 (e.g., LCD), input component 616 (e.g., keyboard, microphone, touch screen on display), and cursor control component 618 (e.g., mouse button).

In various embodiments, computer 600 can execute instruction sequences. In various other embodiments, a plurality of computer systems 600 coupled by communication link 620 (e.g., wireless cell phone network, wireless or wired LAN, PTSN, or various other wireless networks) may perform instruction sequences in coordination with one another. Computer 600 may transmit and receive messages, data, information and instructions, including one or more programs (i.e., application code) through communication link 620 and communication interface 612.

In accordance with some embodiments, various computer programs may be run which identify reliability events that may impact aircraft availability. Operational data, maintenance data, supply data, and other suitable data for aircraft may be collected from many sources. The collected data is preferably formatted for analysis by a computer. In one process, the collected data may be used to calculate metrics for the aircraft. These metrics comprise various variables or parameters of interest with respect to aircraft availability. In another process, trends relating to metrics affecting the availability of the aircraft may be identified. In a further process, a prediction of future aircraft availability can be generated based on the trends.

Figure 14:
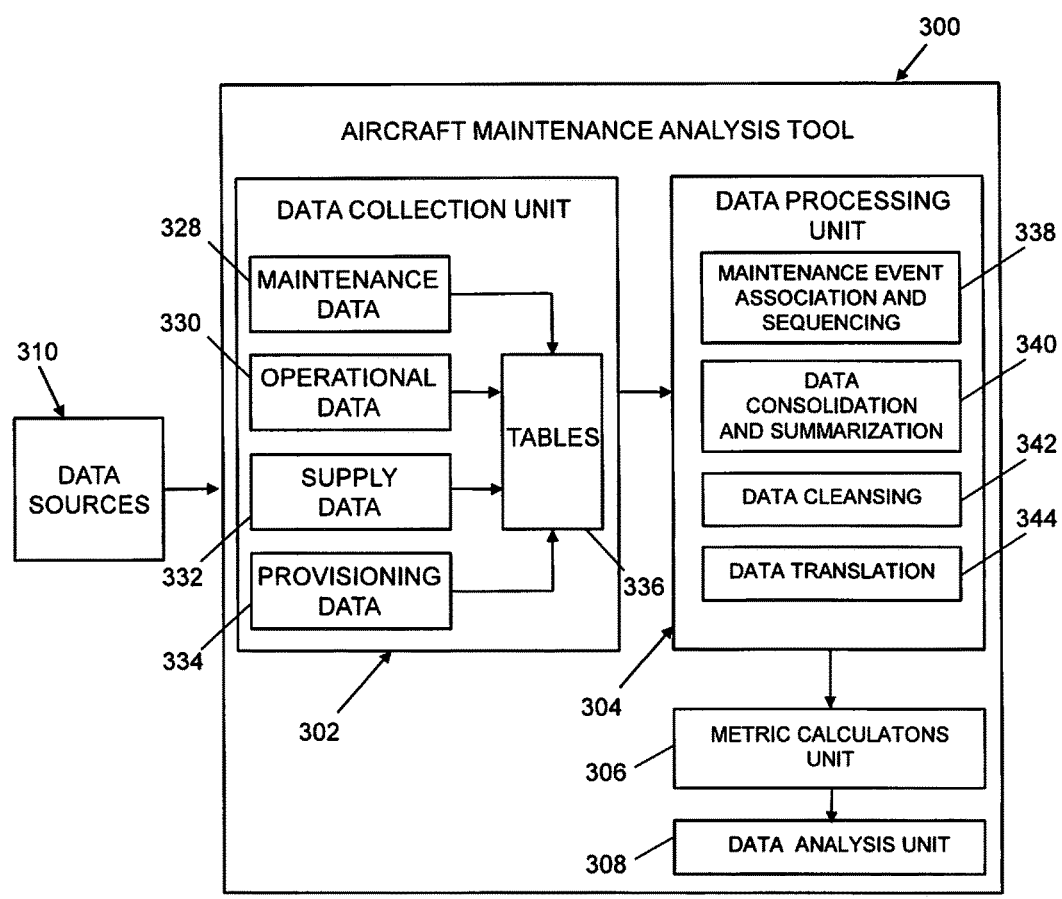
FIG. 14 is a block diagram identifying components of an aircraft maintenance analysis tool in accordance with one embodiment.

For the sake of illustration, FIG. 14 identifies components of an aircraft maintenance analysis tool 300 (i.e., software)

hosted by one or more computers of the type generally depicted in FIG. 13. In accordance with one embodiment, aircraft maintenance analysis tool 300 comprises a data collection unit 302, a data processing unit 304, a metric calculations unit 306, and a data analysis unit 308. Aircraft maintenance analysis tool 300 may receive data from a multitude of data sources 310. For example, data sources 310 may contain data regarding the operation, maintenance, supply, and provisioning of aircraft for which an analysis may be made. Maintenance data 328, in these examples, is data about the maintenance performed on an aircraft. This maintenance may include, actions, such as, for example, non-destructive testing and/or repair of components in the aircraft or on components that may have been removed from the aircraft for repairs or other maintenance operations. Operational data 330 is data about the usage and operation of aircraft. Supply data 332 contains information about components or parts that may be used in the aircraft. Provisioning data 334 is data about the parts themselves. In accordance with one embodiment, the data collection unit 302 stores data from data sources 310 in various tables 336.

More specifically, maintenance data 328 includes maintenance events for parts, as well as data relating to these events. This data may take various forms. For example, maintenance data 328 may include, for example, actions taken to return an item to an operable condition, equipment identification, discrepancy and corrective action reports, when a malfunction is discovered, malfunction reason, repair parts used, applicable serial numbers, maintenance times, location of the work performed, start and/or stop times, and other suitable information. The data in tables 336 may take the form of maintenance forms, depot repair data, operational data, requisition forms, translation codes, squadron status reports, intermediate component lists, asset visibility data, repair and consumable costs, and other suitable types of data.

The data in tables 336 is then processed by data processing unit 304. In these examples, data processing unit 304 may include functions, such as maintenance event association and sequencing 338, data consolidation and summarization 340, data cleansing 342, and data translation 344. Maintenance event association and sequencing 338 may be used to associate the data with any event that has occurred for a part. In other words, every step of a maintenance action may be traceable and linked together based on characteristics of an event. In this manner, events for a part may be placed into a sequence for various types of categories for analysis. Data consolidation and summarization 340 may be used to place data in a format for further analysis. This processing of the data may allow for an identification of trends in which similarities or differences in repair cycles of different repair facilities over a period of time may be identified. Further, this process data may be used to identify progression of a part through a repair cycle and identify the scope and depth of the repair required for the part. The data also may be used to identify current stage of repair for a part. Data cleansing 342 may be performed to place data into a condition that may be used by metric calculations unit 306 and data analysis unit 308. Data cleansing 342 conditions data for analysis. Data translation 344 may place the data in a format that is usable by metric calculations unit 306.

Metric calculations unit 306 contains processes used to identify various metrics for parts. These metrics include, for example, aircraft mission capability and utilization, aircraft cycle time, awaiting parts, awaiting maintenance, turn-around times, repair and scrap rates, supply fill rate, cannibalization rates, no defect rate, total repair cost, mean flight hour between unscheduled maintenance action, mean flight hour between removal, mean flight hour between demand, and other suitable metrics.

Data analysis unit 308 may perform various types of analysis based on metrics generated by metric calculations unit 306. This analysis also may include identifying trends with respect to various parts. In these examples, the data analysis may be performed to identify reliability events that may impact aircraft availability. In accordance with some embodiments, trend analysis may provide the ability to identify the tendency of a metric to increase and/or decrease over a period of time. Trend identification may be used for advanced detection of situations, such as, for example, an increasing failure, removal, maintenance man hour, or beyond capability of maintenance rates. Changes in failure or removal rates can be an indicator of a degrading part. As another example of trend analysis, variances in maintenance man-hour rates or beyond capability of maintenance rates can be an indicator of changes in the abilities of the maintainer, such as improved system knowledge over time or the influx of new maintenance personnel. Changes in these types of metrics can also be attributed to changes in the maintenance processes or changes in the capabilities of support equipment used during maintenance activities. Additionally, these trends may be impacted by part availability and a number of other factors.

Further, data analysis unit 308 may be used to predict future aircraft availability based on the different trends. The propensity of a trend to increase or decrease may be identified by calculating the average slope of a line over time. Predictions may be made by creating a linear projection using the value of slope calculated using historical data and applying that slope factor out to project values or rates at future points in time to anticipate the future needs such as increases and/or decreases in supply, manpower, and/or funding. Predictive models may be used as an evaluation tool to determine what initiatives are worth pursuing based on the potential for improved aircraft availability or cost reductions.

In these examples, data analysis unit 308 may perform various types of analysis including, for example, without limitation, drill down data analysis, data modeling, high driver identification, trend analysis and triggering, improvement opportunity identification, component performance reports, cradle to grave component tracking, squadron performance reports, repair efficiency analysis, repair bill of material listing, life cycle cost analysis, events leading to failure reports, and other suitable analysis.

The illustration of aircraft maintenance analysis tool 300 and the different components are not meant to imply architectural limitations on the manner in which different advantageous embodiments may be implemented. The different units are depicted are functional components that may be implemented in different ways. For example, metric calculations unit 306 and data analysis unit 308 may be implemented as a single software component rather than as two components.

More details concerning aircraft maintenance analysis tools of the type described above can be found in U.S. Pat. No. 8,019,504, the disclosure of which is incorporated by reference herein in its entirety.

The remote expert NDT system disclosed herein provides a standardized, efficient method for transmitting data on damage and malfunctions of aircraft structures and systems for rapid decision-making, and accumulation of statistical data for analyzing, identifying and forecasting damage trends for quality control and product improvement.

In one exemplary scenario, a user (who may be personnel working in an airport ramp area around an aircraft during boarding, servicing and loading activities) may observe an incidence of damage or malfunction. The user may then access a rapid reporting communications device, such as a cell phone, to communicate the observation to an NDT expert at a remote communications hub. A discussion between the ramp area personnel and the NDT expert may take place using the rapid reporting communications device. This results in a decision whether some measure of non-destructive inspection is required.

If a determination is made that the incident is of a minor nature, i.e., does not require NDI, routine documentation may be captured as follows: The cell phone is equipped with image acquisition and transmission capability, as, for example, a cell phone with a digital camera. For record-keeping, the ramp personnel photographs specific areas of the aircraft using the cell phone, such as the tail number for identification, the general damage area, and any further detailed images. The ramp area personnel transmits the images via the cell phone to the ramp supervisor who receives and evaluates them. After evaluating all available evidence, the ramp supervisor makes a decision as to whether the aircraft can fly (i.e., depart) or is in need of some level of repair. Aircraft disposition instructions are received at the ramp/boarding area, pursuant to the aircraft disposition decision issued by the ramp supervisor.

In the case where consultation between ramp personnel and the ramp supervisor determines that NDI measures are required, the next decision concerns whether a simple category of pass/fail NDI tests may be sufficient. If the decision is positive (i.e., YES), then one or more simple NDI test instruments are deployed by ramp personnel. Using the simple NDI test instruments, the ramp personnel attempts to determine if subsurface damage exists. An evaluation of the simple NDI tests determines whether the tests are sufficient to assess whether the potential for subsurface composite damage has been adequately assessed. If the NDI test produces satisfactory results and damage is limited or cosmetic, at this point the ramp personnel may acquire, using the cell phone camera, identifying information, including images of the aircraft tail number, general area of the aircraft, and damaged area. The personnel will then transmit the imagery to the NDT expert, who receives and evaluates the imagery and information as explained above.

In the case where simple NDI tests produce unclear or unsatisfactory results, the NDT expert may decide to deploy extensive and quantitative advanced NDI. This procedure may require, for example, establishing a video and data link between advanced NDI equipment at the ramp location and the NDT expert located at the remote communications hub. During the advanced NDI procedure, data and imagery may be transmitted to the NDT expert, who remotely supervises the procedure and interprets the inspection data. The expert may then evaluate the inspection data and imagery and prepare a damage report, which may be transmitted to the inspection site and stored in a maintenance database of the remote communications hub.

In addition to enabling rapid assessment for repair versus dispatch decisions concerning aircraft, the foregoing system provides means for the archival acquisition of damage and malfunction histories that may be analyzed across aircraft fleets, airline carriers, airport service facilities, components, component suppliers and a myriad of other relational criteria to build statistical databases that may be helpful, for example, to observe trends, identify potential causal effects, improve safety, products and processes, control operating production costs for manufacturers or operating costs for carriers. This process may be carried out in a decision tree structure that accesses a relational database of the information acquired from many accumulated incidents, using various software methods of data mining.

Figure 15:
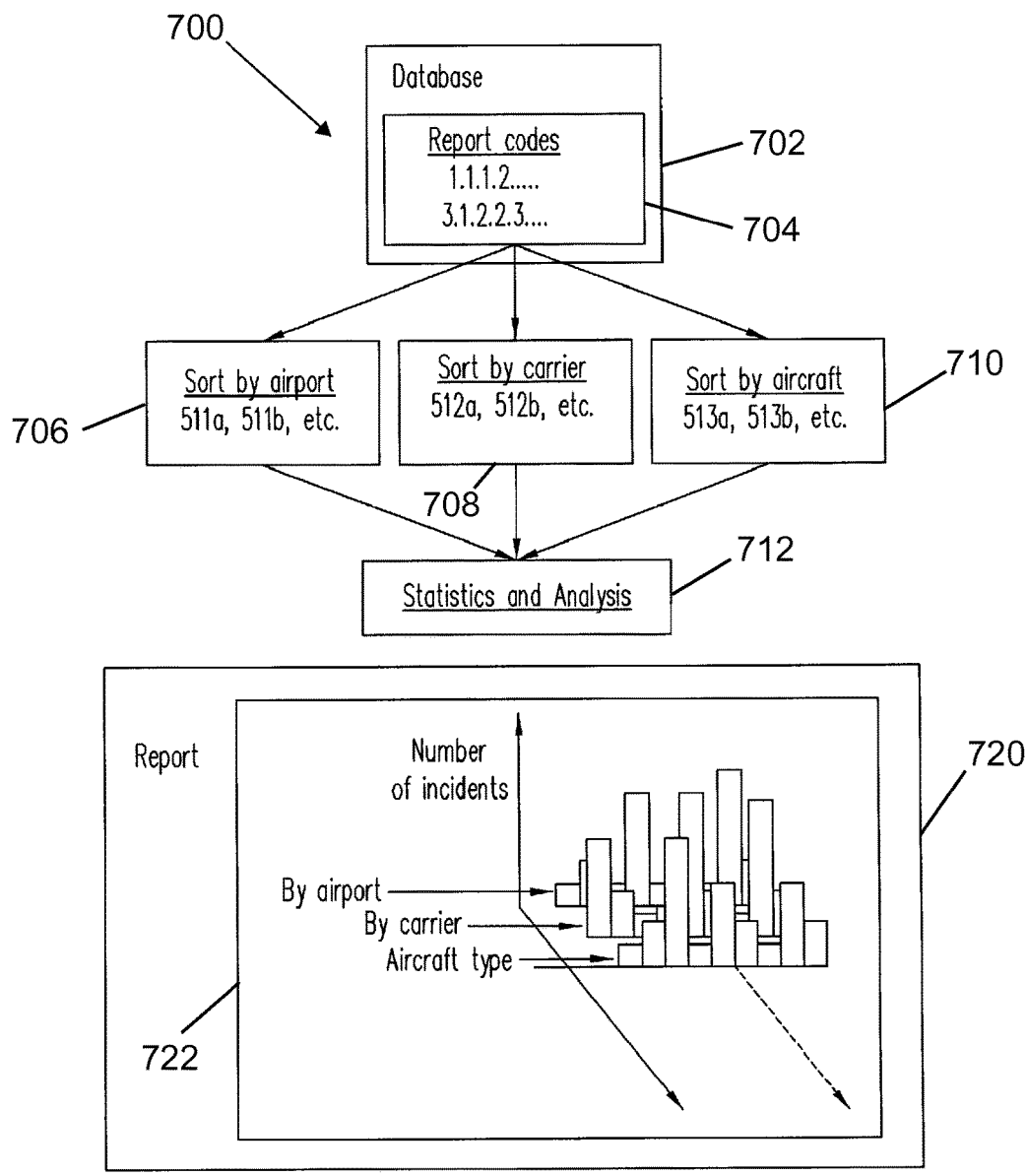
FIG. 15 is a flowchart identifying steps of a method for deriving statistical trends in damage and malfunction incidents in accordance with one embodiment.

FIG. 15 is a flowchart identifying steps of a method 700 for deriving statistical trends in damage and malfunction incidents for analysis and forecasting in accordance with one embodiment. Report codes 704 may be retrieved from a database 702 and sorted according to any appropriate criteria. For example, If the incidence of cargo door damage during loading is sorted by airport (step 706), a histogram may be generated for all airports (e.g., 511a, 511b, etc.), for all carriers (step 708) or a subset of carriers (e.g., 512a, 512b, etc.), for one or more types of aircraft (step 710) (e.g., commuter (513a), medium-range (513b), etc.). Many different statistical analysis methods 712 may be employed, which may also include correlation analysis between categories to search for behavioral trends. The results of the analysis and forecasting may be presented in a report 720, which may include a presentation of data, for example, in histogram form 722 or other forms (such as graphs, tables and text). The report 720 may provide information to identify relationships between damage/malfunction types and rates of occurrence and correlations to conditions that predispose such occurrences. This may help to indicate areas such as procedures, design modification, or training that could beneficially reduce the number of such occurrences, reducing airline carrier costs, delays, inconveniences and supplier warranty costs.

While systems and processes for enabling an off-site NDT expert to interact with an on-site technician have been described with reference to various embodiments, it will be understood by those skilled in the art that various changes may be made and equivalents may be substituted for elements thereof without departing from the scope of the teachings herein. In addition, many modifications may be made to adapt the concepts and reductions to practice disclosed herein to a particular situation. Accordingly, it is intended that the subject matter covered by the claims not be limited to the disclosed embodiments.

The process claims set forth hereinafter should not be construed to require that the steps recited therein be performed in alphabetical order (any alphabetical ordering in the claims is used solely for the purpose of referencing previously recited steps) or in the order in which they are recited. Nor should they be construed to exclude any portions of two or more steps being performed concurrently or alternatingly.

The invention claimed is:

1. A remote expert non-destructive testing system comprising a remote communications hub and a multiplicity of non-destructive testing equipment located at respective testing sites and networked to said remote communications hub by respective communication links, wherein:

the remote communications hub comprises a network server, first and second remote work stations, and a local area network that interconnects the network server and the first and second remote work stations; and the multiplicity of non-destructive testing equipment comprises first non-destructive testing equipment located at a first testing site and second non-destructive testing equipment located at a second testing site, the first and second non-destructive testing equipment being respectively in communication with the first and second remote work stations via the first network server and the local area network,
wherein the first and second non-destructive testing equipment respectively comprise first and second software, and the remote communications hub further comprises a system management server that is connected to the local area network, wherein the system management server is configured to determine when the first and second software need to be upgraded and then send software updates to the first and second non-destructive testing equipment via the local area network and the network server when the first and second software respectively need to be upgraded.

2. The system as recited in claim 1, wherein the remote communications hub further comprises a database server that is connected to the local area network, wherein the database server stores non-destructive testing data acquired by the first and second non-destructive testing equipment.

3. The system as recited in claim 1, further comprising a local positioning system positioned adjacent a test article at the first testing site, the local positioning system comprising a video camera and a laser range meter mounted to a pan-tilt unit and a controller in communication with the first remote work station via the first network server and the local area network.

4. The system as recited in claim 3, wherein the first remote work station is configured to locate the first non-destructive testing equipment relative to the test article at the first testing site.

5. The system as recited in claim 4, wherein the remote communications hub further comprises a database server that is connected to the local area network, wherein the database server stores non-destructive testing data in association with location data representing the location of the first non-destructive testing equipment relative to the test article at the first testing site.

6. The system as recited in claim 1, wherein the first non-destructive testing equipment is mounted to a mobile platform, the system further comprising a remote tracking system in communication with the first remote workstation via the network server of the remote communications hub, wherein the remote tracking system is configured to track a location of the mobile platform and send mobile platform location data to the first remote workstation via the network server.

7. The system as recited in claim 1, further comprising a remote tracking system in communication with the first remote workstation via the network server of the remote communications hub, wherein the remote tracking system is configured to track a location of an expert and send expert location data to the first remote workstation via the network server.

8. The system as recited in claim 1, further comprising a remote data analytics system in communication with the first remote workstation via the network server of the remote communications hub, wherein the remote data analytics system is configured to perform statistical analysis of the non-destructive testing data acquired by the first non-destructive testing equipment, construct a report indicating whether a test article should be taken out of service for repair or not, and send the report to the first remote workstation via the network server.

9. The system as recited in claim 8, wherein the remote data analytics system is further configured to construct a service bulletin and transmit that service bulletin over a network to portable communications devices if warranted in view of the results of the statistical analysis.

10. A remote expert non-destructive testing system comprising a remote communications hub and a multiplicity of non-destructive testing equipment located at respective testing sites and networked to said remote communications hub by respective communication links, wherein:
the remote communications hub comprises a first network server, first and second remote work stations, a first local area network that interconnects the first network server and the first and second remote work stations, a second network server, a system management server, a second local area network that interconnects the second network server and the system management server, and a wide area network that interconnects the first and second network servers; and
the multiplicity of non-destructive testing equipment comprises first non-destructive testing equipment located at a first testing site and second non-destructive testing equipment located at a second testing site, the first and second non-destructive testing equipment being respectively in communication with the first and second remote work stations via the wide area network, the first network server and the first local area network,
wherein the first and second non-destructive testing equipment respectively comprise first and second software, and the system management server is configured to determine when the first and second software need to be upgraded and then send software updates to the first and second non-destructive testing equipment via the second network server and the wide area network when the first and second software respectively need to be upgraded.

11. The system as recited in claim 10, wherein the remote communications hub further comprises a database server that is connected to the second local area network, wherein the database server stores non-destructive testing data acquired by the first and second non-destructive testing equipment.

12. The system as recited in claim 10, further comprising a local positioning system positioned adjacent a test article at the first testing site, the local positioning system comprising a video camera and a laser range meter mounted to a pan-tilt unit and a controller in communication with the first remote work station via the wide area network, the first network server and the first local area network.

13. The system as recited in claim 12, wherein the first remote work station is configured to locate the first non-destructive testing equipment relative to the test article at the first testing site.

14. The system as recited in claim 13, wherein the remote communications hub further comprises a database server that is connected to the second local area network, wherein the database server stores non-destructive testing data in association with location data representing the location of the first non-destructive testing equipment relative to the test article at the first testing site.

15. The system as recited in claim 10, wherein the first non-destructive testing equipment is mounted to a mobile platform, the system further comprising a remote tracking system in communication with the first remote workstation via the wide area network, the first network server and the first local area network, wherein the remote tracking system is configured to track a location of the mobile platform and send mobile platform location data to the first remote workstation.

16. The system as recited in claim 10, further comprising a remote tracking system in communication with the first remote workstation via the wide area network, the first network server and the first local area network wherein the remote tracking system is configured to track a location of an expert and send expert location data to the first remote workstation.

17. The system as recited in claim 10, further comprising a remote data analytics system in communication with the first remote workstation via the wide area network, the first network server and the first local area network, wherein the remote data analytics system is configured to perform statistical analysis of the non-destructive testing data acquired by the first non-destructive testing equipment, construct a report indicating whether a test article should be taken out of service for repair or not, and send the report to the first remote workstation.

18. The system as recited in claim 17, wherein the remote data analytics system is further configured to construct a service bulletin and transmit that service bulletin over a network to portable communications devices if warranted in view of the results of the statistical analysis.

19. A remote expert non-destructive testing system comprising a remote communications hub and a multiplicity of non-destructive testing equipment located at respective testing sites and networked to said remote communications hub by respective communication links, wherein:

- the remote communications hub comprises a network server, first and second remote work stations, a database server, a system management server and a network that interconnects the network server, first and second remote work stations, database server, and system management server;
- the multiplicity of non-destructive testing equipment comprises first non-destructive testing equipment located at a first testing site and second non-destructive testing equipment located at a second testing site, the first and second non-destructive testing equipment being respectively in communication with the first and second remote work stations via the first network server and the local area network and respectively comprising first and second software;
- the database server stores non-destructive testing data acquired by the first and second non-destructive testing equipment; and
- the system management server is configured to determine when the first and second software need to be upgraded and then send software updates to the first and second non-destructive testing equipment via the network server when the first and second software respectively need to be upgraded.

* * * * *